US005763191A

United States Patent [19]
Knoll et al.

[11] Patent Number: 5,763,191
[45] Date of Patent: Jun. 9, 1998

[54] UNIVERSAL BINDING FILM

[75] Inventors: Wolfgang Knoll, Mainz; Franz-Josef Schmitt, Leiwen; Christian Klein; Hans-Joachim Guder, both of Weilheim, all of Germany; Martha Liley, London, United Kingdom; Jürgen Spinke, Kelkheim-Münster, Germany

[73] Assignee: Boehringer Mannheim GmbH, Mannheim, Germany

[21] Appl. No.: 279,715

[22] Filed: Jul. 25, 1994

Related U.S. Application Data

[63] Continuation of Ser. No. 928,915, Aug. 12, 1992, abandoned.

[30] Foreign Application Priority Data

Dec. 12, 1990 [DE] Germany ............... 40 39 677.0
Jun. 11, 1992 [DE] Germany ............... 42 19 159.9

[51] Int. Cl.$^6$ ............... G01N 33/53; G01N 33/543; B05D 3/10; B32B 15/00
[52] U.S. Cl. ............... 435/7.1; 422/68.1; 422/82.05; 427/327; 427/328; 427/402; 428/615; 428/621; 428/624; 435/4; 435/7.5; 436/518; 436/524; 436/525; 436/527
[58] Field of Search ............... 435/7.1, 7.5; 422/68.1, 422/82.05; 436/518, 524, 525, 527, 805, 807, 815, 816, 817; 427/327, 328, 402, 404, 405, 415; 428/615, 621, 624

[56] References Cited

U.S. PATENT DOCUMENTS 4,959,305 9/1990 Woodrum ............... 435/7
5,077,210 12/1991 Eigler et al. ............... 435/176

FOREIGN PATENT DOCUMENTS

| 0112721 | 7/1984 | European Pat. Off. . |
| 0254575 | 1/1988 | European Pat. Off. . |
| 0263184 | 4/1988 | European Pat. Off. . |
| 0295073 | 12/1988 | European Pat. Off. . |
| 0339821 | 11/1989 | European Pat. Off. . |
| 0410280 | 1/1991 | European Pat. Off. . |
| 4039677 | 6/1992 | Germany . |
| 2217447 | 10/1989 | United Kingdom . |
| 9005303 | 5/1990 | WIPO . |
| 9210757 | 6/1992 | WIPO . |

OTHER PUBLICATIONS

Stanker et al "Development of an Immunoassay for Chlorinated Dioxins Based On a Monoclonal Antibody & an Enzyme Linked Immunosorbent Assay (ELISA)" Chemosphere 16 #8/9 (1987) pp. 1635–1639.

(List continued on next page.)

*Primary Examiner*—Ponnathapura Achutamurthy
*Attorney, Agent, or Firm*—Felfe & Lynch

[57] ABSTRACT

The invention concerns a binding matrix containing a carrier material and a solid phase reactant which is adsorbed to this via anchor groups that is capable of binding to at least one free reaction partner wherein the solid phase reactant forms a dilute and essentially laterally homogeneous binding layer on the surface of the carrier material. In addition a method for the determination of an analyte in a sample solution is claimed in which a solid phase reactant is used which is a component of a binding matrix according to the present invention. In this process the specific binding reaction is preferably determined by optical reflection techniques.

58 Claims, 6 Drawing Sheets

OTHER PUBLICATIONS

Bain et al "Modeling Organic Surfaces with Self–Assembled Monolayers" Agnew. Chem. Int. Ed. Engl. 28 #4 (1989) pp. 506–512.

North "Immunosensors: Antibody–Based Biosensors" Trends in Biotechnology 3 #7 (1985) pp. 180–186.

Kalb et al "Binding of Proteins to Specific Target Sited in Membranes Measured by Total Internal Reflection Fluorescence Microscopy", Biochem. 29 (1990) pp. 1607–1613.

Blakenburg, R. et al. "Interaction Between Biotin Lipids & Strepavidin in Monolayers: Formation of Oriented Two–dimensional Protein Domains Induced by Surface Recognition" Biochem. 28 #20 (1979) pp. 8217–8221.

Luo et al "Avidin–Biotin Coupling as a General Method for Preparing Enzyme–Based Fiber–Optic Sensors" Anal. Chem. 61 #10 (1989) pp. 1069–1072.

Bain et al "Comparison of Self–Assembled Monolayers on Gold: Coadsorption of Thiols & Disulfides" Langmuir 5 (1989) pp. 723–727.

Nuzzo et al. "Adsorption of Bifunctional Organic Disulfides on Gold Surfaces", Journal of the American Chemical Society, (1983) 105, pp. 4483–4484.

Ebersole et al. "Spontaneously Formed Functionally Active Avidin Monolayers on Metal Surfaces; a Strategy for Immobilizing Biological Reagents and Design of Piezoelectric Biosensors", Journal of the American Chemical Society, (1990) 112, pp. 3241–3242.

Troughton, E.B., (1988) "Monolayer Films Prepared by the Spontaneous Self–Assembly of Symmetrical and Unsymmetrical Dialkyl Sulfides from Solution onto Gold Substrates: Structure, Properties, and Reactivity of Constituent Functional Groups", Langmuir, vol. 4, pp. 365–385.

Patricia C. Weber, et al. "Structural Origins of High–Affinity Biotin Binding to Streptavidin" Science (Jan. 6, 1989) vol. 242, pp. 85–88.

Richard C. Ebersole et al. "Spontaneously Formed Functionally Active Avidin Monolayers on Metal Surfaces: A Strategy for Immobilizing Biological Reagents and Design of Piezoelectric Biosensors" J. Am. Chem. Soc. (1990) 112:3239–3241.

L. Haussling, Dissertation University Mainz (1991) pp. 15–16 and 21–29.

Janusz W. Sadowski "Review of Optical Methods in Immunosensing" SPIE vol. 954 (1988) Optical Testing and Metrology II pp. 413–419.

P. Bergveld "A Critical Evaluation of Direct Electrical Protein Detection Methods" Biosensors and Bioelectronics 6 (1991) pp. 55–72.

Compound 10

Biotin compound 9

Diphenylhydantoin compound

UNIVERSAL BINDING FILM

This application is a continuation of application Ser. No. 07/928,915, filed Aug. 12, 1992, now abandoned, which was a continuation-in-part of application PCT/EP91/02393 having an international filing date of Dec. 12, 1991.

SUMMARY

The present invention concerns a binding matrix which contains a carrier material and a solid phase reactant which is adsorbed to this via anchor groups that is capable of binding to at least one free reaction partner whereby this solid phase reactant forms a dilute binding layer on the surface of the carrier material.

Molecular recognition reactions involve the stable and specific binding of two molecules which occurs without the formation of a covalent atomic bond. For practical purposes, those reactions are of particular interest which proceed at the interface between a solid carrier material and a liquid environment. For this the surface of the solid carrier material is coated with an immobilizing layer which contains a solid phase reactant. The actual recognition reactions then proceed on this immobilizing layer.

An example of such an immobilizing layer is streptavidin bound to polymerized albumin which in turn readily binds adsorptively to plastic surfaces. This solid phase can be used for a large number of immunological tests by means of binding to biotin or to biotinylated reactants. This binding matrix based on streptavidin/polyalbumin is very well suited to "large" plastic surfaces. However, if the coated surface is reduced in size then the accuracy of the test is diminished. In new test systems—e.g. classical ELISA or determination via optical or electrochemical sensors—there is a growing need for miniaturization.

Streptavidin monolayers are described in publications by Blankenburg et al. (Biochemistry 28 (1989), 8214), and Ahlers et al. (Thin Solid Films 180 (1989) 93–99), which are based on a Langmuir-Blodgett (LB) film. For this, firstly biotin lipid monolayers are produced with the complicated film balance technique which have to be subsequently incubated for ca. 2 hours with a streptavidin solution. An additional disadvantage of these LB films is their limited stability, in particular with regard to drying out.

A further method for producing an immobilized layer on a carrier material is the so-called "self-assembled monolayer" (SAM). Thus Nuzzo and Allara (J. Am. Chem. Soc. 105 (1983), 4481–4483), describe the adsorption of organic disulfides onto gold which leads to a close-packed monolayer. The spontaneous organization of such monolayers (hence the expression SAM) is based on strong specific interactions between the carrier material and the adsorbate. Bain and Whitesides (Angew. Chem. 101 (1989), 522–528), describe SAMs which form by adsorption of long chained thiols onto gold surfaces. Thus a close-packed monolayer is obtained by incubating a gold surface with thiols having the formula

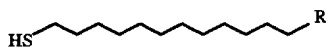

R = Aklyl, Vinyl, Halogen,
Carbonsaure, Ester, Amid,
Nitril, OH, Ether in a dilute organic solution (e.g. 1 mmol/l). These monolayers are stable for several months in a dry state, in water or ethanol at room temperature. Desorption occurs when they are heated to temperatures above 70° C. The stability of the monolayer increases with the length of the aliphatic chain of the thiol. These monolayers are also resistant to dilute acids (e.g. 1N HCl) or to dilute bases (e.g. 1N NaOH) for a certain period (1 to 7 days).

EP-A 0 339 821, discloses polymers for coating metal surfaces which contain thiol groups as a binding mediator to the solid carrier material and amino groups in order to bind a suitable solid phase reactant e.g. biotin and then to bind streptavidin to this. However, even when using these polymers containing thiol groups it is not possible to achieve a strictly homogeneous coating because of their polymeric nature.

A publication by Ebersole et al. (J. Am. Chem. Soc. 122 (1990), 3239–3241), discloses functionally active monolayers of avidin and streptavidin by the direct adsorption of these proteins to gold and silver surfaces. In this process a close-packed streptavidin binding phase is formed which, despite a relatively long incubation period of 20 minutes with a biotinylated binding partner, only yields a very incomplete coating with this binding partner.

Thus in summary it has been established that the binding phases based on monolayers described in the prior art can bind a free reactant either slowly or only with a low coating. The object of the present invention was therefore to at least partially eliminate these disadvantages of the prior art. In particular it is intended to provide a universal binding phase which is as far as possible microscopically homogeneous and which in as short a time as possible can bind as large an amount as possible of a free reactant.

The object according to the present invention is achieved by a binding matrix containing a carrier material and a solid phase reactant which is adsorbed to this via anchor groups that is capable of binding to at least one free reaction partner, wherein the solid phase reactant forms a dilute and essentially laterally homogeneous binding layer on the surface of the carrier material.

In a preferred embodiment the dilute monolayer consists of one type of molecule whereby the surface is not completely covered. The degree of coverage with the solid phase reactant which is a measure for the "dilution", can be expressed as the quotient of the actual thickness of the monolayer divided by the theoretical thickness of the layer for a close packing.

The degree of coverage of the monolayers with the solid phase reactant is less than 100%, preferably 0.1 to 90%, particularly preferably 0.5 to 70% and most preferably 1 to 40%.

The relatively large space between the individual molecules of the solid phase reactant on the surface of the carrier material results in a dispersed layer in the binding matrix according to the present invention in contrast to the close-packed layer of the state of the art. The dilute monolayer on the surface of the binding matrix according to the present invention allows a more rapid binding of the free reaction partner from a liquid phase and is surprisingly characterized by a higher binding capacity.

The carrier material of the binding matrix according to the present invention can have a metal, metal oxide or glass surface. The carrier material preferably has a metal surface, particularly preferably a noble metal surface. The production of a carrier material with a gold surface is carried out for example by evaporating chromium as a binding mediator onto glass whereby a ca. 0.1 to 10 nm thick layer is formed. This chromium layer is subsequently coated with gold to form a gold layer which represents the surface of the carrier material for a binding matrix according to the present invention. It is expedient that this gold layer has a thickness between ca. 10 and 100 nm if the binding matrix is used for surface plasmon resonance. For other applications e.g. as an electrochemical sensor the binding matrix may also be thicker.

The adsorption of the solid phase reactant to the surface of the carrier material is mediated by anchor groups. The type of anchor group depends on the respective surface of the carrier material. Thiol, disulfide or phosphine groups are suitable as anchor groups for a carrier material with a metal surface. Thus for example thiol or disulfide groups are particularly suitable for gold or silver surfaces and phosphine groups for a palladium surface. If the carrier material has a metal oxide surface (e.g. $Al_2O_3$) then a carboxylate or sulfonate group is suitable as the anchor group. With a glass/silicon surface and hydroxylated surfaces, such as $SiO_2$ on Si, $Al_2O_3$ on Al organosilicon compounds are used as anchor groups. Trichlorosilanes are preferably used (Sagiv, J. Amer. Chem. Soc. 102 (1980) 82).

For the adsorption to the solid phase, the anchor group is preferably not attached directly to the solid phase reactant but is instead linked via a spacer molecule, preferably via a flexible spacer molecule, to the solid phase reactant. The spacer molecule particularly preferably contains an alkylene group of the formula $(CH_2)_n$ in which n represents a natural number from 1 to 30, preferably 2 to 30, particularly preferably 2 to 15. One side of the spacer molecule contains the anchor group (e.g. the thiol group or disulfide group) which is suitable for adsorption to the surface of the carrier material. On its other side, facing away from the carrier material, the spacer molecule contains one or several linking groups via which the solid phase reactant or a component thereof is linked to the spacer molecule. These linking groups can be for example an amino or hydroxyl group which is for example linked with a carboxyl group of the solid phase reactant to form an ester or amide group. The spacer molecule can, however, also contain a carboxyl group as the linking group which is then in turn linked to a reactive amino or hydroxyl group of the solid phase reactant.

It should be made clear that there are several ways in which a binding matrix according to the present invention having a dilute monolayer of the solid phase reactant can be produced. Several of these methods are set forth in the following, however, it is not intended to limit the scope of the present invention by this compilation.

However, firstly a close-packed monolayer of a solid phase reactant which is not according to the invention shall be described. Such a layer can be obtained when a alkyl chain having hydroxyl or amino terminal groups is reacted with an activated biotin derivative according to the publication of Bain and Whitesides (Angew. Chem. 101 (1989), 522–528), whereby when 11-hydroxy-undecane-1-thiol is used as the starting material a biotinylated molecule having the following formula is formed:

A measurement of thickness showed that when this molecule is adsorbed to a carrier material with a gold surface until saturation a close-packed monolayer is formed with a coverage of 100% with respect to biotin. In this way a rigid binding matrix is obtained which as such is not in accordance with the present invention and also only has a low binding capacity for a free reaction partner (in this case streptavidin).

In contrast to this, the binding matrix according to the present invention can be produced by using a spacer molecule which is at the same time linked to two or more molecules, preferably 2 molecules, of the solid phase reactant. An example of such a spacer molecule is cystamine which contains a disulfide group as an anchor group and two amino groups as linking groups and thus can be linked to two molecules of an activated biotin whereby a biotinylated molecule having the following formula is formed:

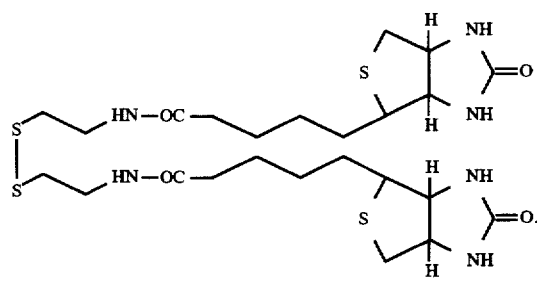

On adsorption to a gold surface this biotinylated molecule forms a binding matrix according to the present invention with a degree of coverage of 30% with respect to biotin and can bind a free reaction partner (streptavidin) with high affinity to form a dense film.

A further possibility of producing a binding matrix according to the present invention is the incorporation of a hydrophilic linker group between the spacer molecule and the solid phase reactant. This linker is in particular a straight-chained molecule with a chain length of 4 to 15 atoms. In this case a linker group is preferred which contains one or several hydrophilic ethylene oxide units preferably between 1 and 5. The hydrophilic linker group is particularly preferably formed from an amino-terminal or hydroxyl-terminal polyethylene oxide.

A further spacer molecule can preferably be incorporated between the hydrophilic linker and the solid phase reactant which comprises an alkylene group of the formula $(CH_2)_n$ and a linking group in which n is a natural number from 2 to 15.

1,8-diamino-3,6-dioxaoctane has proven to be a particularly suitable linker. Thus by incorporation of 1,8-diamino-3,6-dioxaoctane between a $C_{11}$-thiol spacer molecule and biotin, a biotinylated compound of the following formula is formed:

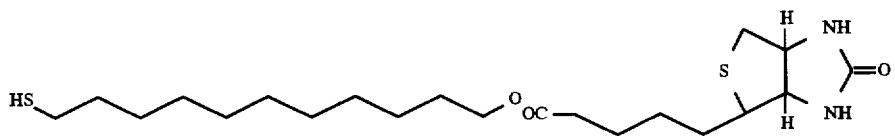

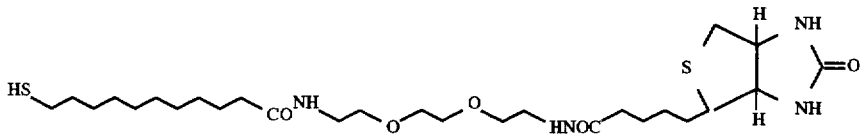

This compound when adsorbed to a gold surface forms a monolayer with a degree of coverage of 19% with respect to biotin and is capable of binding a free reaction partner (streptavidin) with high affinity and within a very short time to form a close-packed film. A binding matrix according to the present invention in which a spacer molecule is linked to the solid phase reactant via a hydrophilic linker group is therefore particularly preferred within the scope of the present invention.

In a preferred embodiment the binding matrix according to the present invention additionally contains further spacer molecules to which no solid phase reactant is bound although they have an anchor group. Such compounds are also denoted dilution molecules in the following. If for example biotinylated and non-biotinylated spacer molecules are used in a ratio of 1:10 to 1:2 then a dilute biotin monolayer is obtained which can bind the free reaction partner at a fast rate and with a high capacity.

Suitable dilution molecules contain an anchor group and a spacer component as well as if desired, a linker molecule, whereby the number of $CH_2$ groups in the spacer molecule does not differ by more than 1–5, preferably not more than 1–2 C atoms from the number of $CH_2$ groups in the spacer molecule which is present bound to the solid phase reactant. Furthermore it has proven to be expedient that the dilution molecule has a minimum chain length of 6 atoms (without anchor group and hydrophilic linker group).

In place of the solid phase reactant at the end of the dilution molecule which is furthest away from the anchor group there is preferably a hydrophilic group such as e.g. a hydroxyl group, carboxylic acid group, a carboxylic acid-ethyl ester group or methyl ester group, a carboxylic acid amide group, carboxylic acid amide group substituted by 1 or 2 methyl or ethyl groups, a sulfonic acid group or a sulfonamide group. It is also preferred that a hydrophilic linker (as defined above) or a part of a hydrophilic linker is bound to the end of the dilution molecule which is furthest away from the anchor group. Consequently a preferred dilution molecule contains an anchor group which can react with the carrier material on one side of the spacer component and a hydrophilic terminal group on the other side.

In a further embodiment of the invention a spacer with a solid phase reactant and a spacer without a solid phase reactant can be linked via a covalent bond. When using gold or silver surfaces this linkage is preferably achieved by a disulfide bridge.

In such mixed monolayers which consist of dilution molecules (spacer molecules without solid phase reactant) and spacer molecules with solid phase reactant the proportion of spacer molecules with solid phase reactant is appropriately 0.1–90 mol-%, preferably 0.5–50 mol-% and particularly preferably 1–40 mol-%.

In all binding films mentioned up to now, the solid phase reactant consists of one component. This is preferably biotin or analogous molecules to biotin such as desthiobiotin, iminobiotin or HABA (4-hydroxy-phenylazo-benzoic acid) which also react with streptavidin.

Further examples of suitable solid phase reactants are antigens or haptens which are capable of binding to an antibody. In this case the solid phase reactant is preferably a hapten with a molecular weight of 100 to 1200. Steroids (such as e.g. digoxin, digoxigenin, cortisol, oestriol, oestradiol, theophylline, diphenylhydantoin, testosterol, bile acids, progesterone and aldosterone); short-chain peptides (such as e.g. argipressin, oxytocin and bradykinin); fluorescein and its derivatives; $T_3$, $T_4$, aflatoxin, atrazine, plant hormones such as e.g. gibberellins; alkaloids (such as e.g. reserpine and ajmalicine) are for example suitable.

Biotin and biotin derivatives, digoxin, digoxigenin, fluorescein and derivatives as well as theophylline are particularly preferably used as the hapten.

On the other hand the solid phase reactant can also consist of several components. This is in particular understood to mean that an inner component of the solid phase reactant is covalently linked to a spacer molecule and is non-covalently bound to the outer component of the solid phase reactant. In this case the outer component of the solid phase reactant is then capable of binding a free reaction partner. The inner component can for example be biotin and the outer component may be streptavidin. Such a binding matrix is on the other hand capable of binding biotinylated reaction partners from a solution since streptavidin has four binding sites for biotin of which at least two are still free.

A binding layer which contains a solid phase reactant comprising two components is then a binding matrix according to the present invention when the outer component of the solid phase reactant, i.e. the component capable of binding to a free reaction partner (i.e. in this particular case streptavidin), forms a dilute layer at the surface of the binding matrix. The inner component of the solid phase reactant preferably forms an undilute layer at the surface of the binding matrix to which the outer component of the solid phase reactant can become attached to form a dilute layer.

Thus a close-packed biotin monolayer with 100% coverage (which does not itself represent a binding matrix according to the present invention) binds streptavidin with a covering density of 27%. This dilute streptavidin layer then in turn represents a binding matrix according to the present invention which can bind a free reaction partner, e.g. a biotinylated antibody, to form a close-packed film. A dilute biotin monolayer which has for example been produced by using a solid phase reactant with spacer and linker (cf. Example 8) and which itself represents a binding matrix according to the present invention for binding free streptavidin can bind streptavidin to form a close-packed film with 100% coverage. The close-packed streptavidin layer which forms in this process does not, however, represent a binding matrix according to the present invention (because it is not flexible) and can bind a reaction partner (e.g. a biotinylated antibody) only to form a film with ca. 10% coverage.

This technique according to the present invention using a dilute bindable solid phase reactant can be extended beyond biotin-streptavidin binding to other binding pairs as for example antibody-antigen etc.

The degree of coverage of the solid phase reactant on the surface of the binding matrix can be determined by measuring the thickness of the binding layer. In this case the measured layer thickness decreases with decreasing degree of coverage of the binding layer. Thus a binding layer with biotin as the solid phase reactant which is described below has a thickness of 0.7 nm, whereby this thickness is less than the calculated length of the molecule of 3.7 nm. A binding layer with streptavidin as the solid phase reactant is also described whose thickness of 0.5 nm is substantially less than the diameter of the streptavidin molecule.

The present invention also concerns a process for the production of a binding matrix according to the present invention. Because of the different nature of the binding matrices according to the present invention, the production processes also differ in detail. Several preferred variants of these production processes are described in the embodiments. In general the process according to the present invention comprises the incubation of the carrier material with a reaction solution in which those molecules are present which form the binding layer of the binding matrix according to the present invention. These molecules have the anchor group and the solid phase reactant on opposite sides (whereby in some embodiments of the present invention not all molecules of the binding layer have to be linked to a solid phase reactant). The solid phase reactant is preferably linked via a spacer molecule to the anchor group. The attachment of the anchor groups to the carrier material from the solution to form the binding matrix according to the present invention is a spontaneous process.

According to a first embodiment of the present invention the incubation of the carrier material with the reaction solution in order to produce the first binding layer preferably takes place under a protective gas and it is expedient to carry this out in an inert solvent which is preferably free of interfering substances e.g. $H_2O$ or $O_2$.

If desired, a further substance can be deposited in a second step by incubation with a second reaction solution in particular if the solid phase reactant consists of several components which are non-covalently linked to one another. The reaction conditions for applying the second and if desired further layers are not critical so that a protective gas does not have to be used and water can be used as solvent.

Surprisingly it was found that short-chained spacer molecules which are coupled to solid phase reactants in combination with hydrophilic diluents form monolayers from aqueous solutions in a self-assembly process, said monolayers having especially advantageous characteristics as a universal binding matrix. The use of such hydrophilic components is advantageous in that the covering of the carrier material may be performed in water or in an aqueous reaction solution. Thus, when the solid phase reactant has strong hydrophilic characteristics one can avoid solubility problems during the building up of the binding matrix. A further advantage of the use of aqueous solvents is that no additional solubilizers (e.g. detergents) have to be present. Such solubilizers may impair the homogeneous build-up of the binding matrix and the biological characteristics of the solid phase reactant and of the binding partner.

A further subject of the present invention is a process for the production of a binding matrix containing a carrier material and a solid phase reactant which is adsorbed to this via anchor groups and is capable of binding to at least one free reaction partner, wherein the solid phase reactant forms a dilute and essentially laterally homogeneous binding layer on the surface of the carrier material, and wherein the carrier material is incubated with an aqueous reaction solution comprising at least a hydrophilic dilution molecule and a solid phase reactant which is joined to the anchor group via a short-chained spacer molecule.

The aqueous reaction solution is water or an aqueous buffer system comprising preferably less than 20% (v/v), more preferably less than 1% (v/v) organic solvent. Most preferably the aqueous buffer system does not contain any additional solubilizers such as organic solvents or detergents.

The carrier material of the binding matrix according to this embodiment of the present invention can have a metal or metal oxide surface. Preferably the carrier material has a metal surface, more preferably a noble metal surface. Thiol, disulfide or phosphine groups are especially suitable as anchor groups for such a carrier material.

For the adsorption to the solid phase the anchor group in this embodiment is not attached directly to the solid phase reactant but is instead coupled via a short-chained spacer molecule, preferably via a flexible spacer molecule to the solid phase reactant. For the purpose of the present invention a short-chained spacer molecule is an alkylene group of the formula $(CH_2)_n$ wherein n represents a natural number from 1 to 6, preferably 1 to 4, more preferably 1 to 3. On its one side the spacer molecule contains the anchor group (e.g. the thiol group or disulfide group) which is suitable for adsorption onto the surface of the carrier material. On its other side, facing away from the carrier material, the spacer molecule contains one or several coupling groups via which the solid phase reactant or a component thereof is coupled to the spacer molecule. These coupling groups can be for example an amino or hydroxyl group which is for example coupled to a carboxylic group of the solid phase reactant to form an ester- or amide-group. The spacer molecule can, however, also contain a carboxylic group as the coupling group which is then in turn coupled to a reactive amino or hydroxyl group of the solid phase reactant. When selecting the spacer molecule a short chain length is essential because the complex of solid phase reactant and spacer is no longer sufficiently water soluble when using a too long hydrophobic chain.

Also in this embodiment of the present invention, the binding matrix can be produced by using a spacer molecule which is at the same time linked to two or more molecules, preferably two molecules of the solid phase reactant.

An example of such a spacer molecule is cystamine which contains a disulfide group as an anchor group and two amino-groups as coupling groups and thus can be coupled to two molecules of an activated biotin (biotin compound 1).

Preferably a hydrophilic anchor group is located between the spacer molecule and the solid phase reactant. This linker is in particular a straight-chained molecule having a chain-length of 4 to 15 atoms wherein the linker chain is preferably consisting of C-atoms and hetero-atoms (preferably N-atoms and/or O-atoms). More preferably is a linker group comprising one or several, preferably between one and five, hydrophilic ethylene oxide units. More preferably the hydrophilic linker group is formed from an amino-terminal and/or hydroxyl-terminal polyethylene oxide.

A further spacer molecule can preferably be incorporated between the hydrophilic linker and the solid phase reactant which comprises an ethylene group of the formula $(CH_2)_n$ and a coupling group in which n is natural number from 2 to 12, preferably from 2 to 8.

An especially suitable linker for the solid phase reactant is 1,8-diamino-3,6-dioxaoctane. Thus, by incorporation of 1,8-diamino-3,6-dioxaoctane between a $C_3$-thiol spacer molecule and biotin, biotin compound 7 is formed.

The aqueous reaction solution for the production of a binding matrix contains in addition to the above-described solid phase reactant a hydrophilic dilution molecule, i.e. a molecule comprising anchor groups to which no solid phase reactant is bound. Suitable dilution molecules comprise an anchor group and a spacer component and optionally a linker group wherein the number of C-atoms of the spacer molecules is preferably from 1 to 6, more preferably from 1 to 4 and most preferably from 1 to 3. When selecting the spacer molecule a short chain-length is preferred, because the dilution molecule is no longer sufficiently water-soluble when using a too long hydrophobic chain.

In place of the solid phase reactant at the end of the dilution molecule which is farthest away from the anchor group there is preferably a hydrophilic group such as e.g. a hydroxyl group, a carboxylic acid group, a carboxylic acid ethyl ester group or methyl ester group, a carboxylic acid amide group, a carboxylic acid amide group substituted by one or two methyl or ethyl groups, a sulfonic acid group or a sulfonamide group. It is also preferred that a hydrophilic linker (as defined above) or a part of a hydrophilic linker is bound to the end of the dilution molecule which is farthest away from the anchor group. Consequently a preferred dilution molecule contains an anchor group which can bind to the carrier material on one side of the spacer component and a hydrophilic terminal-group on its other side.

The overall character of the dilution molecule has to be hydrophilic enough to be soluble in water or in an aqueous buffer. Further, the dilution molecule has to be capable of a spontaneous adsorption to the carrier material. Surprisingly it was found that the dilution molecule may have a significantly shorter chain-length than that of the spacer/linker which is coupled to the solid phase reactant. For example, a dilution molecule having less than 50% of the chain-length of the spacer/linker which is coupled to the solid phase reactant gives better results than a dilution molecule having a chain-length corresponding to that of the spacer/linker at the solid phase reactant.

Thus, the dilution molecule is preferably a novel compound of the general formulae:

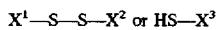

wherein $X^1$, $X^2$ and $X^3$ each represent

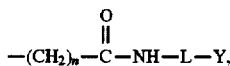

wherein n is a natural number from 1 to 6,

L is a hydrophilic linker group with a chain length from 4 to 15 atoms and

Y is a hydrophilic end group.

For the building-up of a binding matrix according to the present invention also a mixture of several of the above compounds may be used.

An especially preferred example of a short hydrophilic dilution molecule is 2-mercaptopropionic acid-2-(2-hydroxyethoxy) ethyl amide (compound 10).

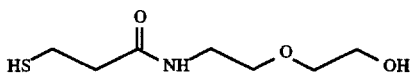

According to a further embodiment of the present invention a spacer having a solid phase reactant and a spacer having no solid phase reactant may be coupled via a covalent bond. When using gold and silver surfaces this coupling preferably is enacted via a disulfide bridge.

A preferred embodiment of this production process is shown in the examples. Generally the process of the present invention comprises incubating the carrier material with an aqueous reaction solution wherein the molecules are present which form the binding layer of the binding matrix of the present invention. These molecules comprise the anchor group and the solid phase reactant at opposite sides, wherein—as discussed above—not all molecules of the binding layer are coupled to a solid phase reactant. The solid phase reactant is coupled to the anchor group via a spacer molecule. The adsorption of the anchor groups to the carrier material from the solution which results in the formation of the binding matrix of the present invention is a spontaneous process.

The incubation of the carrier material with the aqueous reaction solution in order to produce the first binding layer preferably takes place under a protective gas, in water or an aqueous buffer and without addition of interfering substances such as organic solvents or detergents.

As discussed above, a further substance can be attached in a second step by incubation with a second reaction solution in particular if the solid phase reactant consists of several components which are non-covalently bound to each other.

Thus, a further subject of the present invention is a process wherein the binding matrix resulting from the adsorption of a solid phase reactant comprising anchor groups to the carrier material is incubated with one or several further substances capable of binding the binding matrix, whereby a solid phase reactant is produced, consisting of several non-covalently attached components. The lateral binding layer produced according to the process according to the present invention is microscopically homogeneous and can for example be determined by surface plasmon microscopy (B. Rothenhäusler and W. Knoll, Surface Plasmon Microscopy, Nature, Vol. 332, No. 6165, p. 615–617 (1988); W. Hickel, B. Rothenhausler and W. Knoll, "Surface Plasmon Microscopic Characterisation of external surfaces", J. Appl. Phys. (1989), p. 4832–4836; W. Hickel, W. Knoll "Surface Plasmon optical characterisation of lipid monolayers at 5 µm lateral resolution", J. Appl. Phys. 67 (1990), p. 3572, ff.). At a resolution of 5 µm there are no measurable differences in thickness.

The present invention in addition concerns a process for the determination of an analyte in a sample solution by means of a specific binding reaction between at least two reactants having bioaffinity, one of which is present coupled to a solid phase and the other partner or partners are free, whereby a solid phase reactant is used which is a component of a binding matrix according to the present invention.

In such a process the fact that the free binding partner carries a marker group enables the detection of the binding of the free reaction partner to the solid phase reactant. The labelling is usually with an enzyme or with a fluorescent or luminescent component. This allows an indirect optical observation of the binding and hence enables an exact quantitative determination.

In principle the binding can be determined optically, electrochemically and also via heat tonality or formation of mass. Potentiometric and amperometric methods come into particular consideration as electrochemical techniques such as those which are described in "Biosensors", Turner, Karube, Wilson (eds.), Oxford Press, 1987, or Bergveld, Biosensors & Bioelectronics 6, 55–72 (1991). Determinations by means of the electrical conductivity or change in capacitance are also feasible as electrochemical techniques.

However, the detection of the binding is preferably carried out by optical and in particular optical reflection techniques by which means the increase of the layer thickness of an extremely thin layer of the carrier-bound reactant caused by binding of the free binding partner can be observed. A review of these techniques is given in Sadowski: "Review of optical methods in immunosensing," SPIE, Vol. 954 Optical testing and Metrology II (1988), 413–419.

A particularly preferred optical reflection method is the detection of the binding by surface plasmon resonance. In this method the analytical component is composed of a transparent dielectric material which is coated with a very thin metallic conducting layer which carries the solid phase reactant. This analytical component is often denoted optical immunosensor. Examples of such optical immunosensors are described in EP-A 0 112 721 U.S. Pat. equivalent No. 4,931,384), in EP-A 0 276 142 and in EP-A 0 254 575 (U.S. Pat. equivalent No. 4,992,385). The immunosensor described in example 4 is, however, particularly preferred for the quantitative detection of the binding to the solid phase. The principle of such an immunosensor is proposed in detail in DE 40 24 476 and reference is herewith made to this disclosure.

A further specific aspect of the binding film according to the invention is based on the fact that one can use biotin derivatives such as desthiobiotin as the solid phase reactant which have a significant lower binding affinity to streptavidin than biotin. (The binding constant of desthiobiotin/ streptavidin is $10^{12}$ whereas the binding constant of biotin/ streptavidin is $10^{15}$). Thus, when using such a lower affinity solid phase reactant it is possible to displace bound streptavidin by addition of a solution comprising a higher affinity reactant (e.g. biotin) so that in this way the universal binding film may be used repeatedly.

As described above one can use a solid phase reactant which has a rather low binding affinity to the free reaction partner. In this case it is possible to regenerate the binding matrix by removing the reaction partner which is coupled to the solid phase by adding a further free reactant which has a higher binding affinity to said coupled reaction partner than the solid phase reactant.

Thus, a further subject of the present invention is a method wherein subsequent to the determination of an analyte the binding matrix is regenerated by removing the free reaction partner bound to the solid phase reactant from the binding matrix by adding a further free reactant. Preferably the further free reactant has a higher affinity to the reaction partner bound to the solid phase reactant than the solid phase reactant. Examples for suitable pairs of solid phase reactant and free reactant are desthiobiotin and biotin or correspondingly two haptens having only a low chemical difference and thus consequently have a somewhat different binding affinity to a given antibody.

For the practice of immuno-assays using a regenerable desthiobiotin binding phase it is advantageous to use desthiobiotinylated antibodies or antibody fragments or desthiobiotinylated (poly)-haptens.

The binding matrix produced by the process of the present invention can be used as a regenerable layer.

curve 1: thickness of the biotin layer curve 2: dependence of the increase in thickness caused by streptavidin on the mole fraction x of biotin $$x = \frac{C_{biotin\ compound\ 5}}{C_{biotin\ compound\ 5+diluting\ molecule}} \quad :2$$

C: molar concentration

Figure 3:
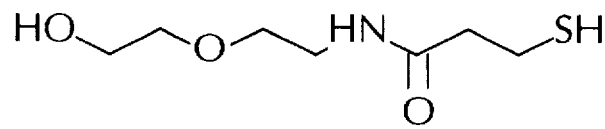
Figure 3C:
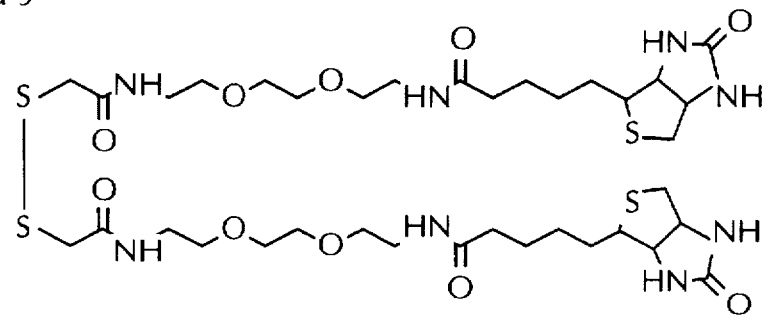
Figure 3C:
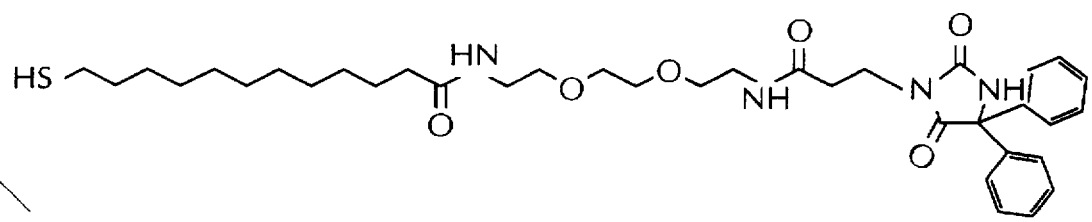
Figure 3A:
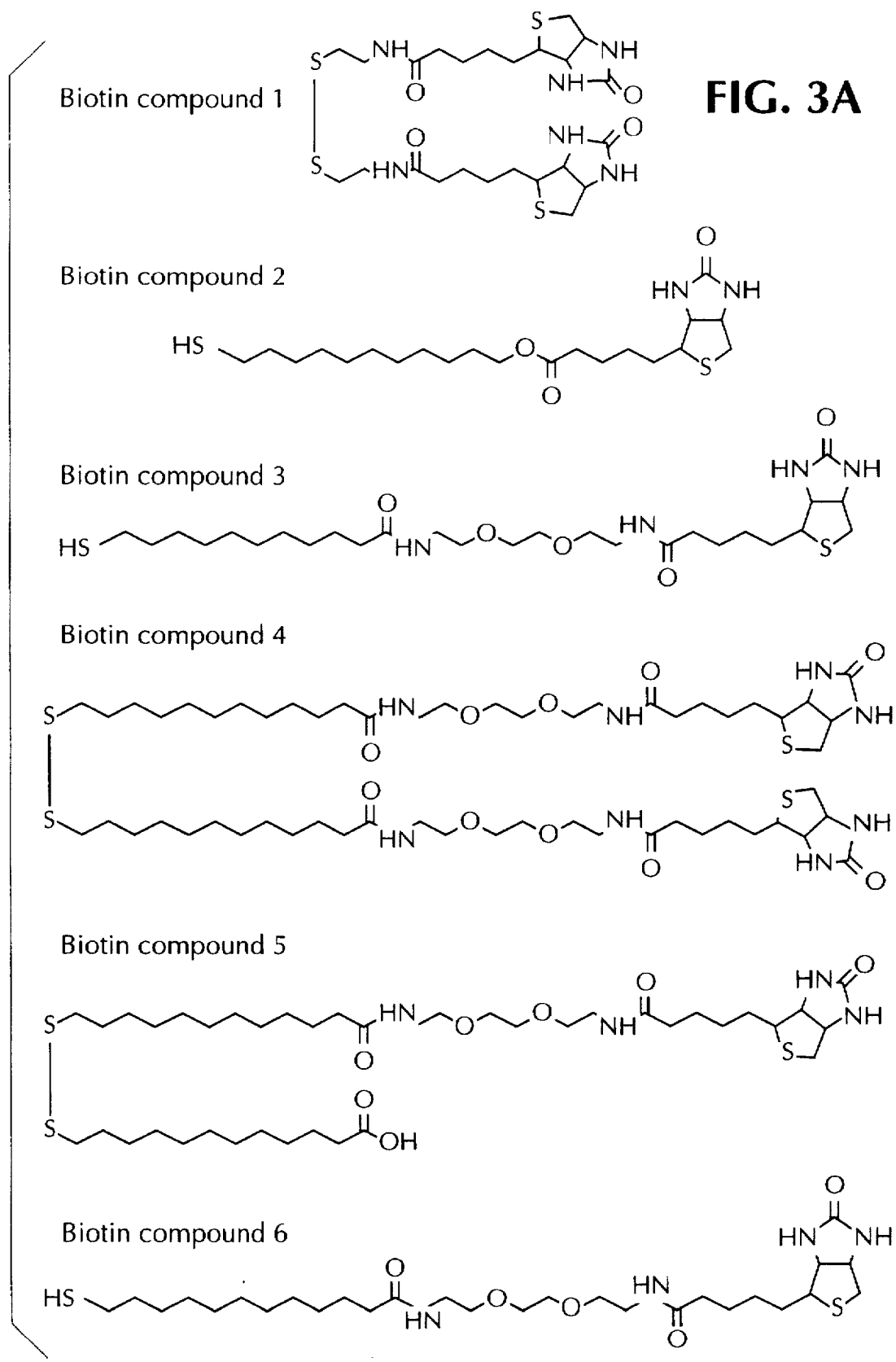
Figure 3B:
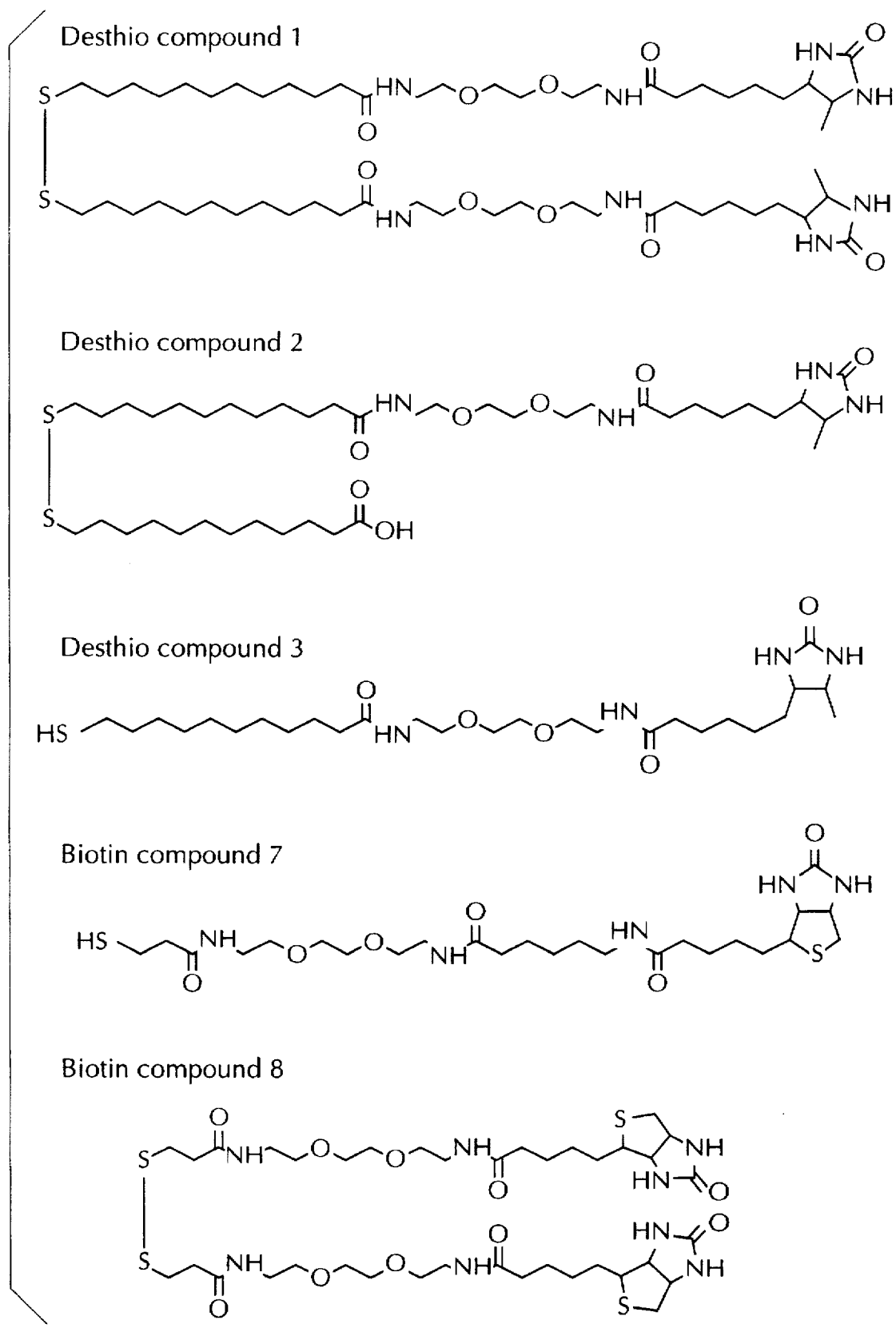

FIG. 3 shows a list of the biotin compounds, biotin derivatives and a diphenylthiohydantoin compound produced according to the present invention.

EXAMPLE 1

Synthesis of bis-biotinoylcystamine (Biotin Compound I)

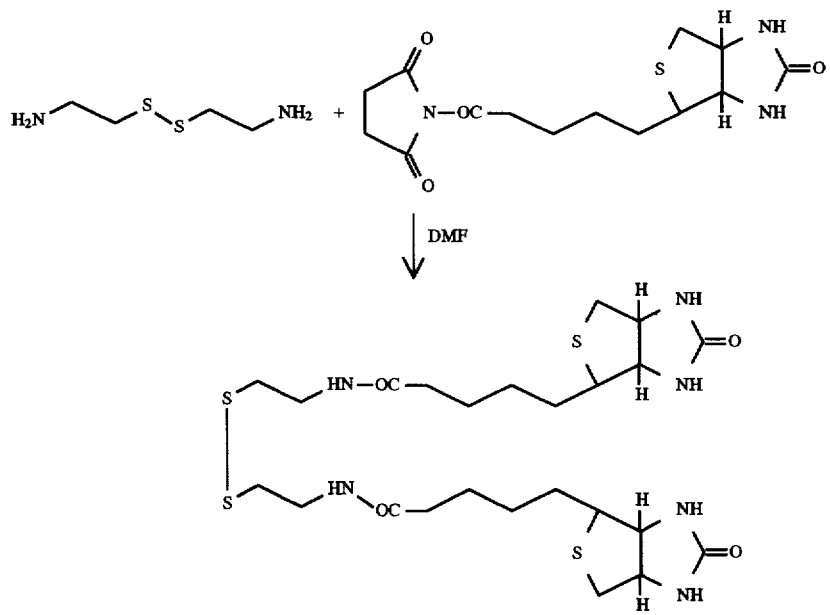

Biotin-N-hydroxysuccinimide ester was added to a solution of cystaminium dichloride and triethylamine in dimethyl formamide (DMF). The reaction mixture was stirred overnight at room temperature. After the reaction was completed the precipitate which formed was filtered off, dried with an oil pump and recrystallized from acetone. The target compound was obtained in a 40% yield.

EXAMPLE 2

Synthesis of biotin (11-mercapto)undecanylester (Biotin Compound II)

The corresponding Bunte salt was synthesized from bromoundecanol (Merck) by boiling the ethanolic solution for 4 hours under reflux and slowly adding dropwise a saturated aqueous sodium thiosulfate solution. The salt crystallizes out of the solution on cooling and was purified by recrystallization from ethanol.

The symmetric disulfide was prepared in 98% yield from this Bunte salt by boiling with an aqueous solution of thiourea which had been adjusted with hydrochloric acid to pH 1. It then crystallizes out of the reaction mixture on cooling.

The disulfide together with biotin and 10 mol % 4-dimethylamino-pyridine (DMAP) in DMF was dissolved by warming and the esterification was initiated by addition of dicyclohexylcarbodiimide (DCCI) dissolved in DMF at −15° C. After 5 hours the preparation was brought to room temperature and stirred for a further 18 hours. After the reaction was completed the DMF was removed in an oil pump vacuum at room temperature and the residue was purified by flash chromatography. 11,11'-bisbiotinylester-undecyl-1,1'-disulfide was obtained in 13% yield and the corresponding monosubstituted product was obtained in 23% yield.

The biotinylated disulfide was then reduced with dithiothreitol (DTT) (Aldrich) in boiling methanol under an argon atmosphere. After the reaction was completed (24 h) the reaction mixture was evaporated to dryness and the disulphidothreitol which formed as well as excess DTT was removed by extraction with a small amount of water. The mixture was then separated by flash chromatography and the desired product was isolated in 80% yield.

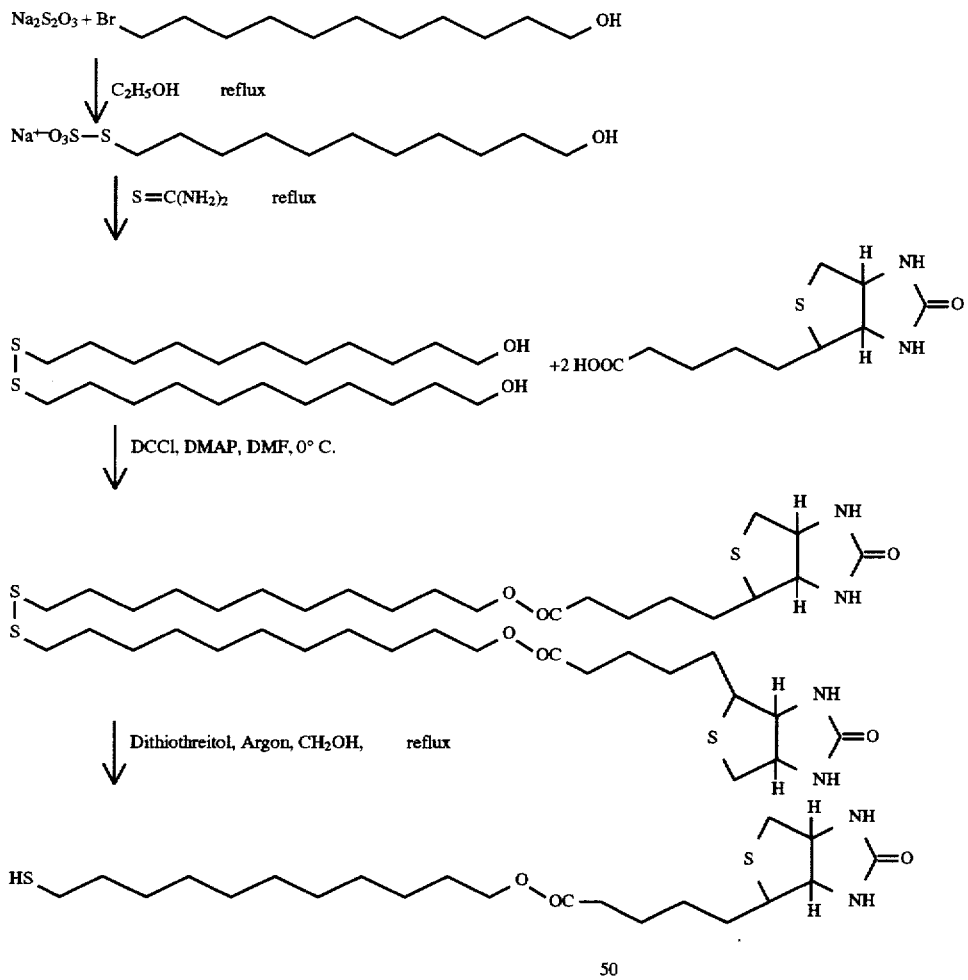

EXAMPLE 3

Synthesis of 11-mercaptoundecanoic acid-(8-biotinoylamido-3,6-dioxyoctyl)amide (Biotin Compound 3)

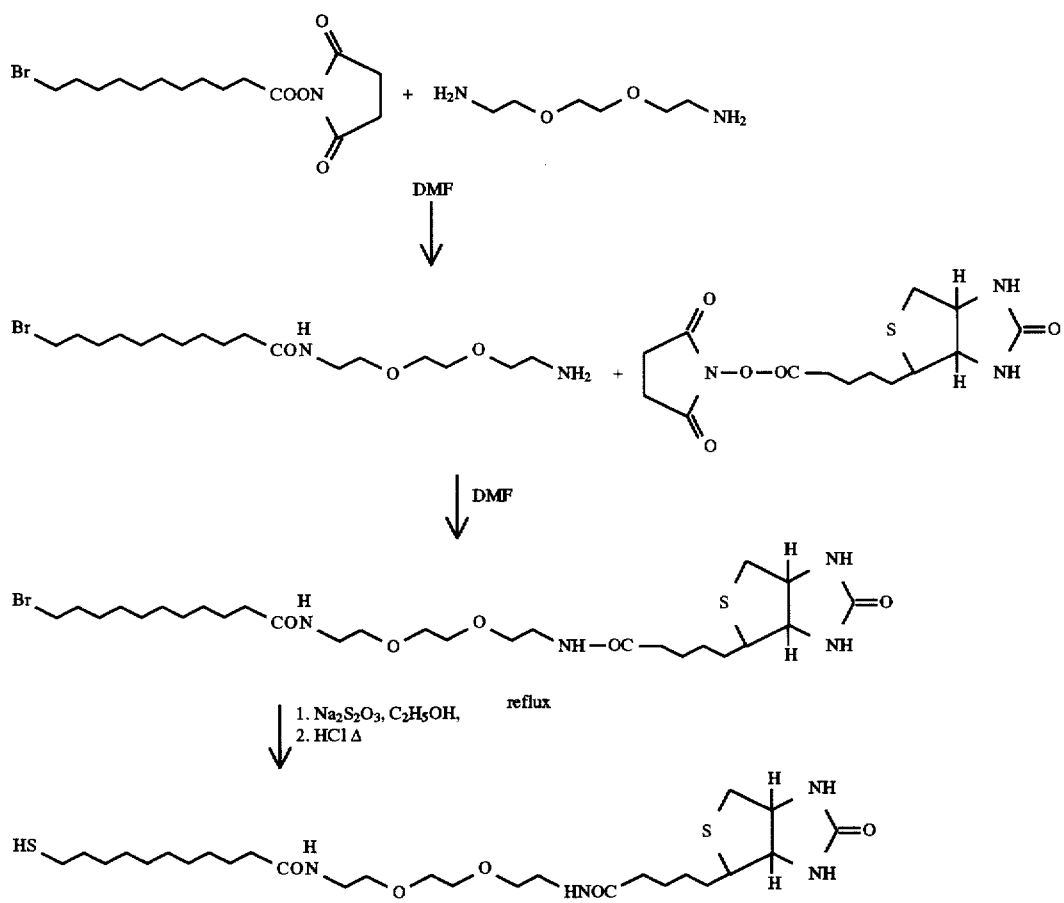

The active ester of 11-bromoundecanoic acid was reacted in the cold with excess 1,8-diamino-3,6-dioxaoctane in DMF solution. After the reaction was completed the precipitated N-hydroxysuccinimide was filtered off and the excess amine was removed together with the DMF in an oil pump vacuum.

The intermediate stage obtained was then reacted with biotin active ester again in DMF. The alkylbromide which formed was isolated after completion of the reaction by flash chromatography (CHCl$_3$/CH$_3$OH:1/1).

The crude product was converted to the Bunte salt (see example 2) and subsequently hydrolysed with 1N hydrochloric acid under argon. The solution was hot filtered in order to remove the sulphur which formed. Subsequently the filtrate was evaporated to dryness and the crude mercaptan was extracted with chloroform/ethanol, the extract was evaporated and isolated by means of flash chromatography (CHCl$_3$/CH$_3$OH:1/1). The desired product was obtained in a 3% yield.

EXAMPLE 4

Production of the Biotin Monolayer 1 from the Biotin Compound 1

Microscope slides made of high index glass SF57 with vapor deposited chromium (1 nm) as an adhesive agent and vapor deposited gold (41 nm) served as the solid carrier. The biotinylated disulfide (from example 1) is used as a 6×10$^{-4}$ mol/l (M) solution in CHCl$_3$/EtOH 1:1. The microscope slide is incubated for 2 hours in the reaction solution under an argon protective gas atmosphere, it is subsequently thoroughly rinsed with pure solvent and dried in a stream of argon. When the coated sample is incorporated in a modified Kretschmann apparatus (FIG. 1) it can be characterized against air as well as against aqueous media.

Figure 1:
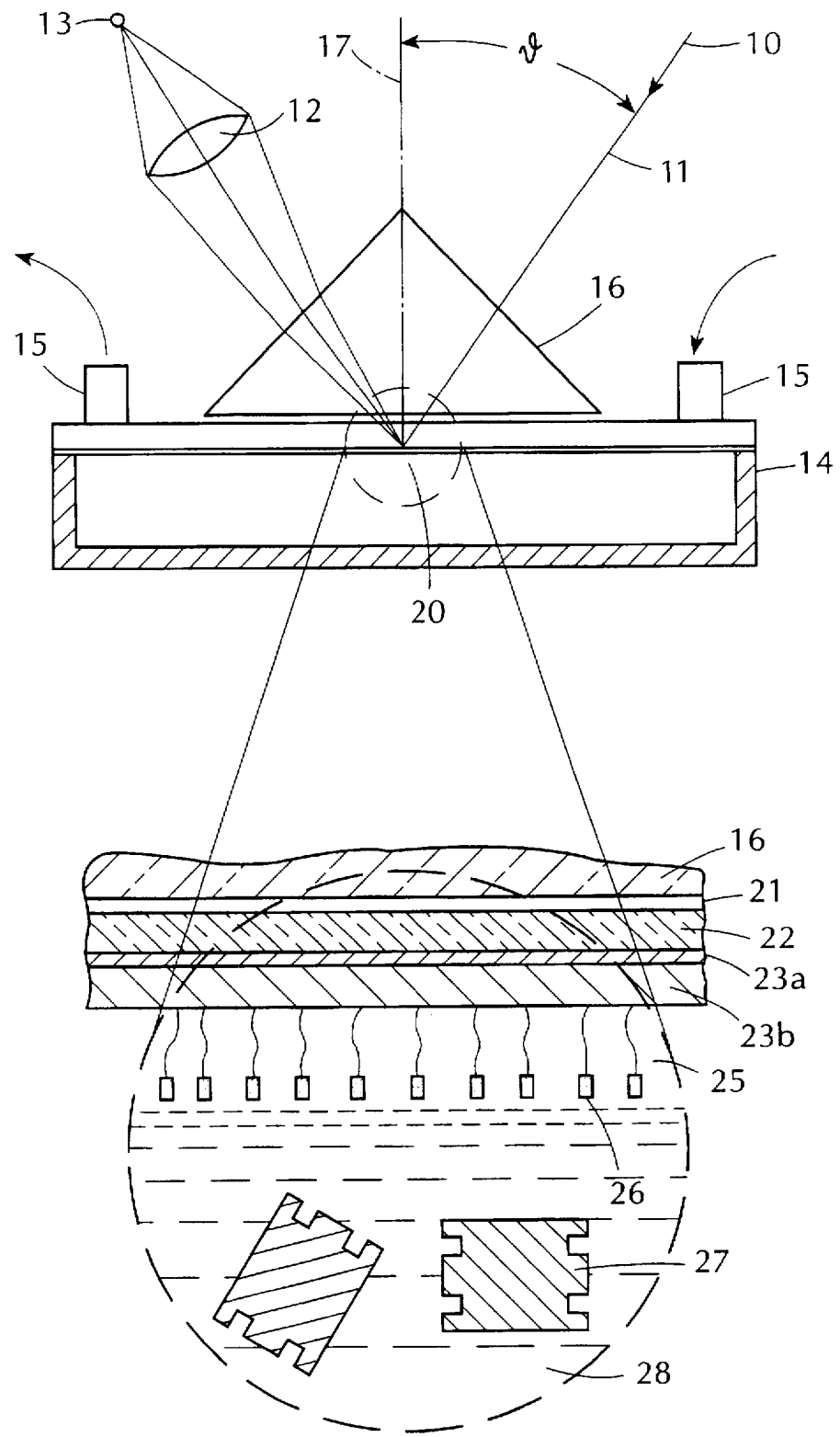
FIG. 1 is a schematic representation of a measuring device which can be used to determine the binding of a free reaction partner to the solid phase.

FIG. 1 shows a diagram of a measuring device for the optical reflectivity determination of the binding of the free reaction partner to the solid phase.

This optical reflection measuring device contains a laser 10. The primary ray 11 emitted by the laser is directed onto the test region 20 at an angle v to the normal of surface 17. An image of the reflected light is formed by a converging lens 12 on the diode 13 which is located in the focal plain.

In addition the measuring device contains a prisma 16 in the Kretschmann configuration and a flow cuvette 14 with entry and exit apertures 15 for the test solution.

The test region 20 consists of a prisma 16 in the Kretschmann configuration, a dielectric, optically transparent carrier layer 22 and a thin metal layer 23a, 23b which is evaporated onto the carrier layer 22. The thin layer of index liquid 21 links the prisma 16 without optical refraction with the optically transparent carrier layer 22 since it has the same refractive index as these two components. In the present case 23a represents the chromium layer mentioned above and 23b represents the evaporated gold layer. 25 represents the spacer molecule which mediates the binding of the solid phase reactant 26 to the gold surface via anchor groups. 27 represents the free reaction partner which is capable of binding to the solid phase reactant and is present in the test phase 28.

With the aid of the Fresnel equations the reflection at the interfaces can be calculated and fitted to the PSP spectroscopy data whereby one obtains a value for the "optical thickness" ($=n^2 \times d$, with n=refractive index and d=thickness) for each layer. If it is assumed that the refractive index for thiolalkanes is n=1.45 then this results in a thickness of 0.5 nm for the adsorbed disulfide. Comparisons with the theoretical value of about 1.6 nm indicate a very incomplete coverage of the surface.

Thus with a ca. 30% coverage of the surface, a "dilute" biotin film is present.

EXAMPLE 5

Streptavidin Binding to the Biotin Monolayer 1/ Production of the Streptavidin Monolayer 1

In order to investigate the reactivity of the biotinylated immobilizing layer the 0.5M aqueous NaCl solution (as reference) is replaced by a $\sim 5 \times 10^{-7}$M streptavidin solution.

The subsequent molecular recognition reaction by streptavidin attains a saturation value of 3.0 nm increase in thickness within an hour. This was based on a refractive index of the protein of n=1.5. The true optically effective refractive index is presumably lower since the interstices of the adsorbed protein molecules are filled with water (n=1.33). If this finding is taken into account the increase in thickness which was found compares quite well with the radiographic values for finely crystalline streptavidin (d=~4.5 nm).

EXAMPLE 6

Production of the Biotin Monolayer 2 from the Biotin Compound 2

The preparation was carried out largely according to example 4. Differences were only with regard to the thiol adsorption to the solid carriers. Thus the concentration of the solution in this case was $4 \times 10^{-4}$ mol/l and the incubation lasted 6 hours.

The value for the thickness of the thiol layer obtained against air was 3.0 nm and against the aqueous environment 3.2 nm. Taking into account an error in the measurement of ca.±0.2 nm and possible deviations of the refractive index of the aqueous subphase this thickness agrees very well with the theoretical value of about ~2.8 nm.

In this case a close-packed biotin film is present with a coverage of ca. 100%.

EXAMPLE 7

Binding of Streptavidin to the Biotin Monolayer 2/ Production of the Streptavidin Monolayer 2

The binding of streptavidin can also be monitored on-line via the displacement of the (flank of) the resonance curve so that kinetic data are also available.

If one assumes a monoexponential time course for the increase in thickness by adsorption, then the following is obtained for the dependence of the reflected intensity on time:

$$I = I_\infty [1 - \exp(-t/\tau)]$$

$I_\infty$: intensity after $t = \infty$
$\tau$: time constant

The time constant $\tau$, in which the adsorption approaches by up to 1/e the saturation value, is about 13 minutes in this experiment.

The resulting streptavidin layer is 0.8 nm which corresponds to a very incomplete coverage with protein. The homogeneity of the layer can be monitored by PSP microscopy with the result that no unevenness was found. Thus the protein accumulates as a layer which although too thin is nevertheless uniform (with respect to the lateral resolution of about 5 µm).

In this case a "dilute" streptavidin film is present with a coverage of ca. 27%.

EXAMPLE 8

Production of the Biotin Monolayer 3 from the Biotin Compound 3

The biotinylated thiol with spacer from example 3 was adsorbed from a $1.25 \times 10^{-4}$M solution. The preparation conditions were otherwise analogous to example 4.

After completion of the protein adsorption and characterization of the layer system against the aqueous environment the sample was thoroughly rinsed with 0.5M NaCl solution and dried under a nitrogen stream. After renewed PSP spectroscopy against air the sample could again be exposed to an aqueous environment in order in this way to detect possible changes caused by the change in environment and the rinsing.

The resulting biotinylated thiol layer had a thickness of 0.7 nm against air as well as against the aqueous subphase. This value is not at all comparable with the theoretical value of ~3.7 nm so that the molecules are indeed scattered and form a very incomplete layer.

In this case a "dilute" biotin film is again present with a ca. 19% coverage.

EXAMPLE 9

Binding of Streptavidin to the Biotin Monolayer 3/ Production of the Streptavidin Monolayer 3

The adsorption of streptavidin was extremely rapid in this case. Assuming, the same monoexponential time course for the increase in thickness one obtains in this case a time constant $\tau$ of only 1 minute.

The streptavidin layer attains an overall thickness of 3.1 nm and under PSP microscopy appears superficially covered with unspecifically adsorbed protein aggregates. Rinsing with the corresponding subphase and drying does not damage the layer system so that the thickness (against air) remains almost constant at 3.0 nm. After the cuvette is filled again with aqueous subphase the film now appears microscopically homogeneous.

EXAMPLE 10

Binding of a Biotinylated Antibody to the Streptavidin Monolayers 2 and 3

As a tetrameric protein streptavidin has four binding sites for biotin/biotinylated molecules. After attachment to the immobilizing layer there should according to geometric considerations be two binding sites available for further recognition reactions oriented towards the aqueous subphase. This was investigated with a biotinylated antibody against TSH, the corresponding non-modified antibody (as reference) and the corresponding antigen TSH as sample. The immunological determination reaction was carried out as described in example 2 of EP-A 0 344 578. The biotinylated antibody adsorbs from a $1 \times 10^{-6}$M aqueous solution to various prepared streptavidin layers. The results obtained in this case appear to be very dependent on the respective thickness and thus on the packing density of the streptavidin layer.

Thus when the biotinylated antibody is adsorbed to a close-packed streptavidin monolayer 3 from example 9 of 3.0 nm only a small increase in thickness of 0.5 nm is obtained. This process is accompanied by an initial decrease in thickness, presumably caused by the detachment of streptavidin which has not been attached firmly enough. The subsequent increase in thickness occurs with a time constant $\tau\sim 3$ minutes.

However, if the biotinylated antibody is adsorbed under analogous conditions to the streptavidin monolayer 2 from example 7 of 0.8 nm then this results in a very much stronger effect with a total increase in thickness of 5.1 nm. On closer inspection of the kinetics one observes an initial slight increase in thickness and then the very much stronger adsorption. In this case the kinetics must be characterized by a biexponential function. The first time period yields a time constant $\tau\sim 5$ minutes.

The close-packed streptavidin monolayer 3 binds the biotinylated antibody more slowly than the "dilute" streptavidin monolayer 2. In addition the "dilute" streptavidin monolayer 2 has a substantially higher binding capacity per unit surface. Thus the measurement effect per time which is achievable is substantially larger with the "dilute" streptavidin film.

b) 12-mercapto-dodecanoic acid 12.2 g of the product from 11a) is dissolved in 200 ml absolute and degassed methanol, 100 ml 1N NaOH is added and it is boiled for 3 hours under reflux. After cooling to room temperature, the reaction mixture is poured into an icebath of 400 ml ice water, 20 ml conc. HCl and 600 ml ether. The ether phase is removed, extracted by shaking 3× with 300 ml $H_2O$ each time, 1× with 100 ml saturated NaCl solution and dried over $Na_2SO_4$. After filtering off the desiccant, the solvent is drawn off.

Yield: 12.3 g

TLC: $R_f$=0.68 (silica gel; ethyl acetate/petrol ether 19/1+ 1% acetic acid)

c) Bis-dodecanoic acid-disulfide 12.0 g of the product from 11b) is suspended in 170 ml ethanol and a solution of 6.3 g iodine in 200 ml ethanol is added dropwise while stirring vigorously. The addition is terminated as soon as a yellow solution is formed which no longer decolourizes. Subsequently 550 ml ether and 350 ml $H_2O$ is added, the aqueous phase is removed and again washed with ether. The combined ether phases are shaken with saturated NaCl solution and dried over $Na_2SO_4$. The residue which remains after filtration of the desiccant and removal of the solvent is recrystallized from acetone.

Yield: 10 g (86% of theory)

TLC: $R_f$=0.57 (silica gel; ethyl acetate/petrol ether 19/1+ 1% acetic acid)

TABLE 1

| Binding film | Degree of coverage | Hydrophilic spacer on biotin | Binding capacity | Binding kinetics |
|---|---|---|---|---|
| Biotin monolayer 1[a] | 30% | none | binds streptavidin to form a dense film, | |
| Biotin monolayer 2[b] | 100% | none | binds streptavidin to form a film with 27% coverage | $\tau = 13$ min. |
| Biotin monolayer 3[a] | 19% | yes | binds streptavidin to form a close-packed film | $\tau = 1$ min. |
| Streptavidin monolayer 2[a] | 27% | — | binds biotinylated Ab to form a close-packed film | $\tau = 3$ min. |
| Streptavidin monolayer 3[b] | 100% | — | binds biotinylated Ab to form a film which is covered by ca. 10% | $\tau = 5$ min. |

[a]: according to the present invention
[b]: not according to the present invention

EXAMPLE 11

Synthesis of bis-dodecanoic acid-disulfide (The Synthesis is Carried out under Inert Gas ($N_2$))

a) 12-mercapto-dodecanoic acid methyl ester 2.3 g (0.1 mol) sodium is dissolved in 200 ml absolute and degassed methanol. The resulting solution is cooled with ice. 7.1 ml (0.1 mol) thioacetic acid and then 14.4 g (50 mmol) bromododecanoic acid are added to this and the solution is boiled for 5 hours under reflux. After cooling to room temperature, 15 ml conc. HCl is added and boiled for 3 hours under reflux. Subsequently, after cooling, 300 ml ether is added and the ether phase is extracted by shaking 3× with $H_2O$, 1× with saturated NaCl solution (100 ml of each). After drying the organic phase over sodium sulphate the solvent is drawn off.

Yield: 12.2 g

TLC: $R_f$=0.86 (silica gel; ethyl acetate/petrol ether 19/1+ 1% acetic acid)

EXAMPLE 12

Synthesis of Bis-(biotinamido-3,6-dioxaoctyl)-dodecanoic acid amide disulfide (Biotin Compound 4)

1.38 g (3 mmol) of the product from example 11c) and 1.76 g (7 mmol) 2-ethoxy-N-ethoxycarbonyl-1,2-dihydroquinoline (EEDQ) are dissolved in a mixture of 150 ml THF and 150 ml DMF, then a solution of 2.25 g (6 mmol) biotinoyl-1,8-diamino-3,6-dioxaoctane (biotin-DADOO) in 40 ml DMF is added dropwise. The reaction mixture is then heated for 3 hours at 50° C. Subsequently it is concentrated in a vacuum and the residue is taken up in 100 ml chloroform and extracted by shaking 2× with 100 ml $H_2O$ each time. After drying over $Na_2SO_4$, the solvent is drawn off and the residue is chromatographed on silica gel (flash chromatography, mobile solvent: chloroform/methanol 9/1).

TLC: $R_f$=0.31 (silica gel; chloroform/methanol 8/1)

MS: m/e=1175 (pos. FAB)

EXAMPLE 13

Synthesis of S-(biotinamido-3,6-dioxaoctyl)-dodecanoic acid amide-S'-dodecanoic acid disulfide (Biotin Compound 5)

The preparation is identical to example 12.
Yield: 300 mg (9% of theory)
TLC: $R_f$=0.05 (silica gel; chloroform/methanol 8/1)
MS: m/e=817 (neg. FAB)

EXAMPLE 14

Synthesis of biotinamido-3,6-dioxaoctyl-12-mercaptododecanoic acid-amide (Biotin Compound 6) (The synthesis is carried out under inert gas)

300 mg (0.3 mmol) of the product from example 12 and 0.5 g (3.3 mmol) dithiothreitol (DTT) is dissolved in 100 ml absolute and degassed methanol and stirred under an inert gas atmosphere for 10 hours. The reaction mixture is subsequently evaporated to dryness, the residue is taken up in methylene chloride and shaken with $H_2O$. The organic phase is dried over $Na_2SO_4$, then concentrated by evaporation and the residue is purified by flash chromatography (silica gel; methylene chloride/ethanol 1/1).

TLC: $R_f$=0.27 (silica gel; chloroform/methanol 8/1)

EXAMPLE 15

Desthiobiotin-N-hydroxy-succinimide ester

A solution of 1.8 g (15.5 mmol) N-hydroxysuccinimide in 40 ml dioxane was added to a solution of 3 g (14 mmol) desthiobiotin (Sigma) and 3.5 g (17 mmol) N,N'-dicyclohexylcarbodiimide in a mixture of 40 ml DMF and 40 ml dioxane while stirring vigorously. It was stirred for 4 hours at 20° C. whereby a fine white precipitate formed which was filtered off after completion of the reaction (monitored by TLC). The filtrate was evaporated in a vacuum, taken up with a small amount of ethyl acetate/DMF 4/1 and allowed to stand for 16 hours at 4° C. In this process further precipitate was formed which was filtered off. This process was repeated several times until no further precipitation was observed. The concentrated filtrate was then taken up in a small amount of ethanol and the product was precipitated by addition of diisopropyl ether. After filtration the filtrate was allowed to stand for 16 hours at 4° C. during which further precipitate formed and was filtered off. After drying in a vacuum at 50° C., a white finely crystalline product was obtained.

Yield: 1.6 g (37%)
TLC (silica gel 60): eluant ethyl acetate/methanol=6/4 RF=0.75

EXAMPLE 16

D-desthiobiotinoyl-1,8-diamino-3,6-dioxaoctane, desthiobiotin-DADOO

A solution of 1.6 g (5 mmol) desthiobiotin-N-hydroxysuccinimide ester was added slowly dropwise to a solution of 7.5 ml (50 mmol) 1,8-diamino-3,6-dioxaoctane in 50 ml dioxane and the reaction mixture was stirred for 16 hours. After the reaction was completed, the mixture was evaporated on a rotary evaporator to form an oil, part of the excess DADOO was washed out with ethyl acetate/ether and the remainder was purified by column chromatography on silica gel.

Silica gel 60, eluant ethyl acetate/methanol 6/4+10% $NH_3$.
TLC: same eluant, RF=0.3
Yield: 0.8 g (50%)

EXAMPLE 17

Bis-(desthiobiotinamido-3,6-dioxaoctyl-)dodecanoic acidamide disulfide Desthiobiotin compound 1

A solution of 1.6 g (5 mmol) desthiobiotin-DADOO (6), 2.3 g (0.5 mmol) bis-dodecanoic acid-disulfide (example 11c), 0.74 g (5.5 mmol) 1-hydroxy-benzotriazole and 1.14 g (5.5 mmol) N,N'-dicyclohexylcarbodiimide in 50 ml dimethylformamide is stirred for 24 hours at 20° C. After the reaction is completed (monitored by TLC) the reaction mixture is evaporated to an oil on a rotary evaporator and purified by flash chromatography on silica gel (eluant: chloroform/methanol 9/1).

TLC: silica gel 60, eluant chloroform/methanol 9/1, RF: 0.4
Yield: 0.25 g (5%)

EXAMPLE 18

S-(desthiobiotinamido-3,6-dioxaoctyl)-dodecanoic acid-S'-dodecanoic acid-disulfide Desthiobiotin compound 2

This compound is obtained as a white amorphous powder from the flash chromatography of the reaction mixture from example 17.

TLC: silica gel 60, eluant chloroform/methanol 9/1, RF=0.3
Yield: 0.8 g (20%)

EXAMPLE 19

12-mercapto-(desthiobiotinamido-3,6-dioxaoctyl) dodecanoic acid-amide Desthiobiotin compound 3

A solution of 200 mg (0.2 mmol) of the compound from example 17 and 2 g (13 mmol) dithiothreitol in 50 ml methanol was heated for 36 hours under reflux. After cooling the solvent was removed on a rotary evaporator and the residue was taken up in chloroform. Subsequently it is shaken with water frequently enough that no more dithiothreitol is detectable in TLC. The chloroform phase is dried over sodium sulphate and evaporated in a high vacuum. The purification was carried out by flash chromatography on silica gel, eluant: chloroform/isopropanol 18/2.

TLC: silica gel 60, eluant: chloroform/methanol 9/1, RF=0.35; yield: 60 mg (30%)

EXAMPLE 20

Diphenylhydantoin-N-propionamido-3,6-dioxaoctyl-12-mercapto-dodecanoic acid-amide Diphenylhydantoin compound In analogy to example 16, diphenylhydantoin-N-propionyl-DADOO is obtained from diphenylhydantoin-N-propionic acid (Cook et al., Res. Communications in Chemical Pathology and Pharmacology 5, (1973), p. 767); and 1,8-di-amino-3,6-dioxaoctane. In analogy to example 13, the corresponding mixed disulfide is obtained from diphenylhydantoin-N-propionyl-DADOO and bis-dodecanoic acid-disulfide according to example 11c); after cleavage with DTT diphenylhydantoin-N-propionamido-3, 6-dioxaoctyl-12-mercapto-dodecanoic acid is obtained.

EXAMPLE 21

Synthesis of bis-(hydroxyphenylazo-benzoylamido-3,6-dioxaoctyl)-dodecanoic acid-disulfide [bis-(HABA-DADOO)-dodecanoic acid-amide-disulfide)

The synthesis is carried out analogous to example 12 with 1.4 g of the product from example 11c and 2.4 g [2-(4-hydroxyphenylazo)-benzoyl]-1,8-diamino-3,6-dioxaoctane (HABA-DADOO)

TLC: Rf=0.65 (silica gel; ethyl acetate/methanol 4/1)

The synthesis of HABA-DADOO is carried out analogous to example 16 from HABA-OSu and DADOO (diamino-3, 6-dioxaoctane). HABA-OSu is prepared analogous to example 15 from HABA and N-hydroxysuccinimide.

TLC (HABA-DADOO): Rf=0.52 (silica gel; butanol/ glacial acetic acid/water 10/3/5)

TLC (HABA-OSu): Rf=0.89 (silica gel; butanol/glacial acetic acid/water 10/3/5)

EXAMPLE 22

Synthesis of (hydroxyphenylazo-benzoylamido-3,6-dioxaoctyl)-12-mercaptododecanoic acid-amide.

(The synthesis is carried out under inert gas)

The synthesis is carried out analogous to example 14 with 200 mg of the product from example 21.

TLC: Rf=0.68 (silica gel; ethyl acetate/methanol 4/1)

EXAMPLE 23

Production of biotin monolayers from the biotin compound 5 and bis(11-hydroxyundecyl)disulfide The coating is carried out according to example 4. Microscope slides made of high index glass LA SF N 9 on which gold (50 nm) was evaporated serve as the solid carrier.

The unsymmetrical disulfide biotin compound 5 carrying a biotin molecule (example 13) and the symmetrical Bis(11-hydroxyundecyl)disulfide carrying no biotin molecule (intermediate stage in example 2) were used. Both compounds each have 2 spacers $(CH_2)_{11}$.

| Mixtures | Mole fraction biotin compound 5 | Mole fraction biotin in relation to the spacer | degree of coverage [ca. %] |
|---|---|---|---|
| "Mixture" 1 (pure biotin compound 5) | 1.0 | 0.5 | 50 |
| Mixture 2 | 0.6 | 0.3 | 30 |
| Mixture 3 | 0.4 | 0.2 | 20 |
| Mixture 4 | 0.2 | 0.1 | 10 |
| "Mixture" 5 (pure bis-(11-hydroxyundecyl)disulfide | 0.0 | 0.0 | 0 |

The total concentration of the components in the individual mixtures is in each case $5*10^{-4}$ mol/l in ethanol.

The microscope slide is incubated for 6 hours with the solution under an argon protective atmosphere, subsequently it is rinsed with pure ethanol and dried in an argon stream. The thickness of the adsorbed monolayer containing biotin is determined analogous to example 4.

Figure 2A:
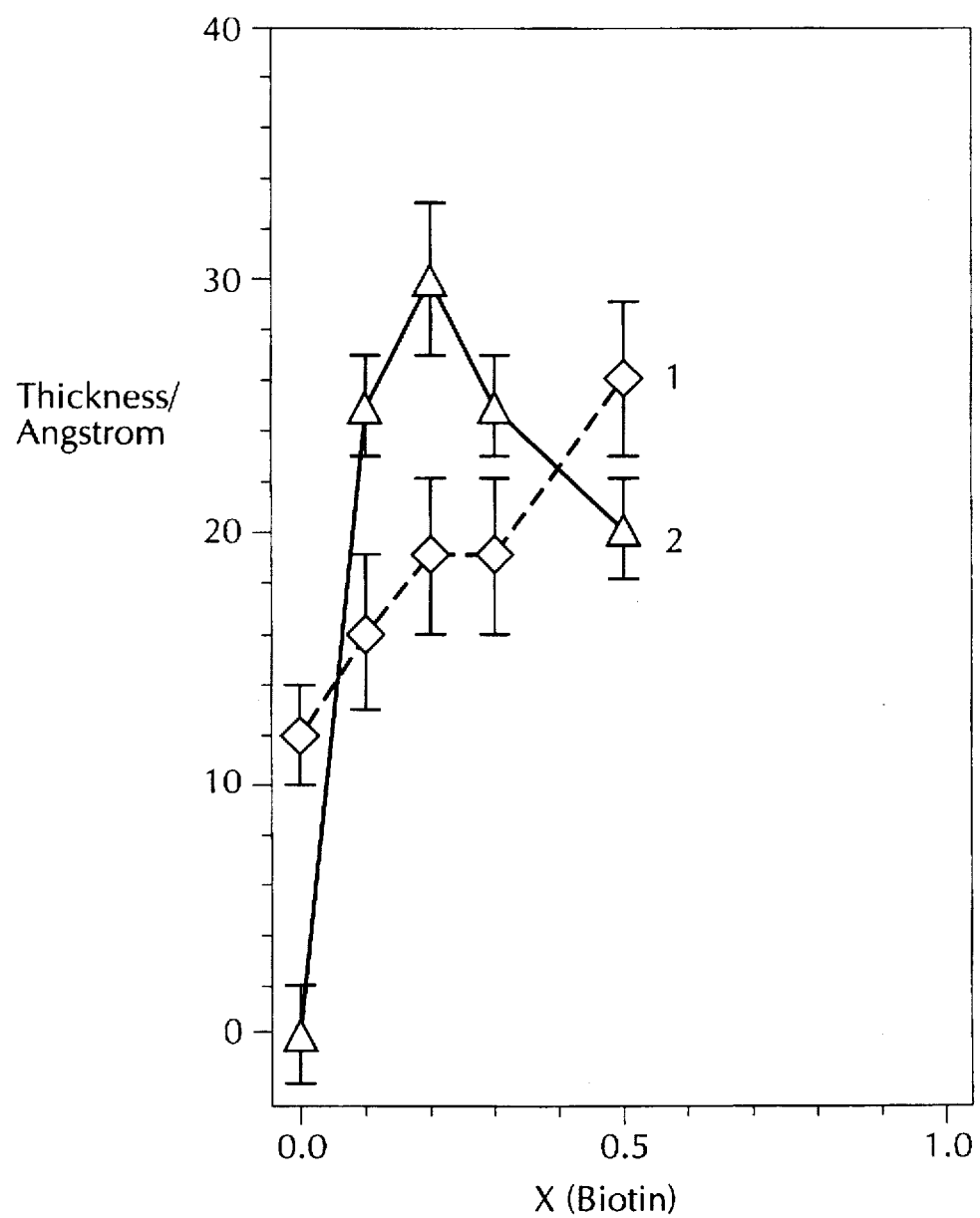
FIG. 2 shows the thickness of binding matrices which are produced by combining a component with solid phase reactants and a diluting molecule as well as the thickness of the streptavidin which is bound to this (example 23 and 24)
Figure 2B:
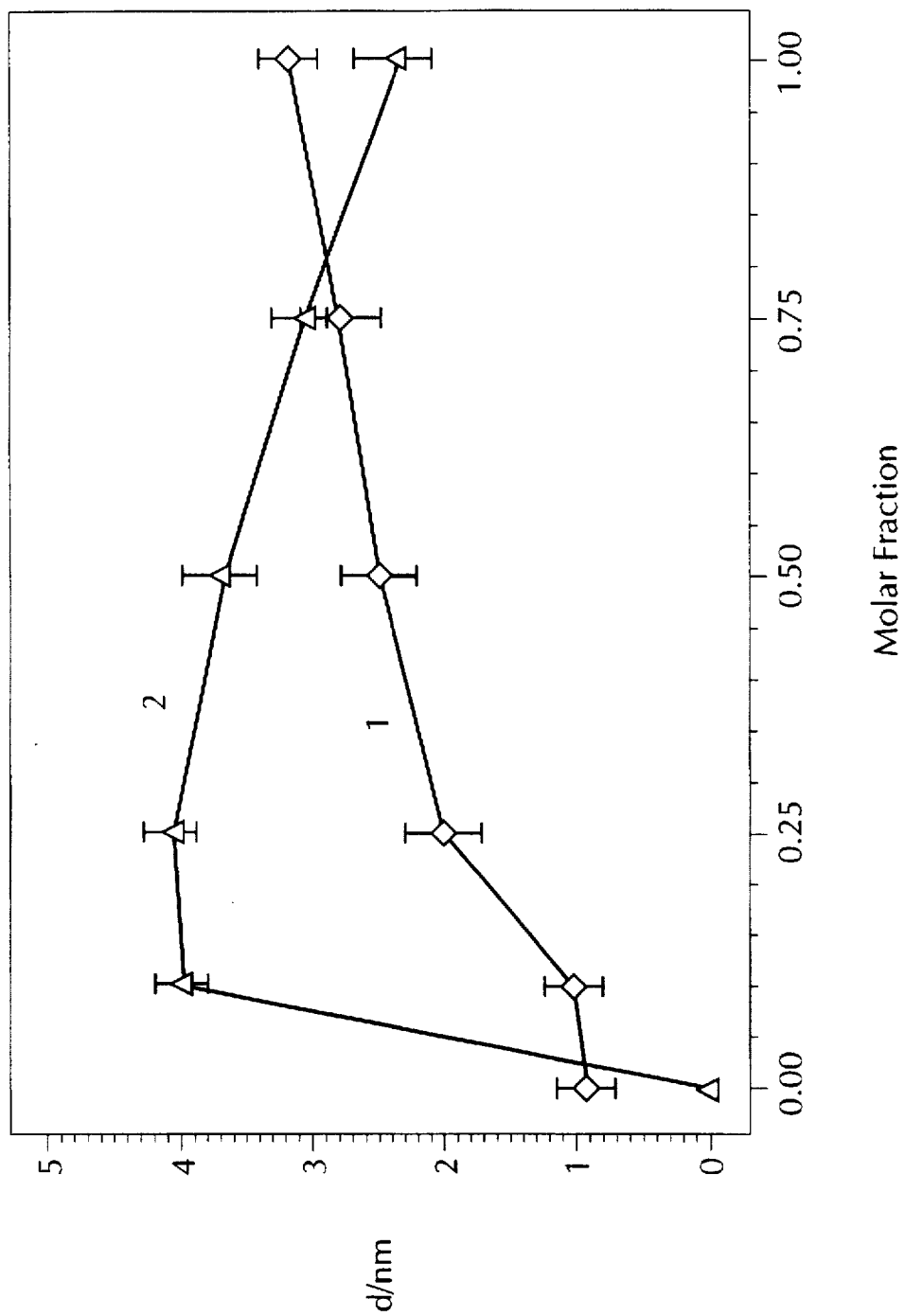

Assuming a refractive index of 1.45 this results in the thicknesses of the adsorbed monolayer shown in FIG. 2. A thickness of 260 nm is obtained for the "mixture" 1; i.e. the pure monolayer of the biotin compound 5. If this is compared with the theoretical value of ca. 250 nm which derives from a portion of ca. 360 nm for the part of the disulfide carrying the biotin and ca. 130 nm for the part which carries no biotin, then the surface is covered with a dense monolayer. Since only half of the spacer molecules are linked to a biotin, the coverage with biotin is 50%.

A dense coverage of the biotin-free disulfide is obtained for the "mixture" 5; a decreasing thickness is obtained for the mixtures 2–4 which implies that a portion of the biotin compound 5 is present corresponding to the mixing ratio in the incubation solution.

EXAMPLE 24

Binding of Streptavidin to the Monolayer Carrying Biotin from Example 12

The monolayers carrying biotin obtained in example 23 are incubated with streptavidin analogous to example 5. The saturation values for the increase in thickness caused by streptavidin binding are shown in FIG. 2. At a mole fraction of 0.1–0.5 of biotin one observes a very high streptavidin binding capacity. Dense streptavidin films result with a coverage between 67% and 100%. The binding kinetics are very fast with half-times of 1–2 min.

EXAMPLE 25

Synthesis of 1-tert.butyloxycarbonyl-1,8-diaminodioxaoctane, (mono-BOC-DADOO)

A solution of 109 g (0.5 mol) Di-tert.butyldicarbonate in 450 ml dioxane is slowly added to a solution of 142 g (1 mol) 1,8-diamino-3,6-dioxaoctane (DADOO) in 900 ml dioxane/water (1/1 v/v). After the addition the mixture is stirred for a further 1.5 hours at 20° C., subsequently the solvent is distilled off and the residue is taken up in 1 l ethyl acetate/water (1/1 v/v). After removing the aqueous phase, the organic phase is extracted twice with 100 ml 0.1N HCl each time. The aqueous phases are pooled, the pH value is adjusted with dilute sodium hydroxide solution to pH 9 to 10 and the solution is subjected to a liquid-liquid extraction in a perforator. After extracting for 8 hours with 750 ml ethyl acetate the solvent is removed and the residue is dried in a high vacuum.

Yield: 32 g (26%)

TLC: silica gel 60,

Eluant: butyl acetate/water/ammonium hydroxide=30/15/5,

RF=0.45

EXAMPLE 26

Synthesis of 1-(biotin-aminocaproic acid)-(1,8-diamino-4,6-dioxaoctane)-amide, (biotin-X-DADOO)

A solution of 0.9 g (2 mmol/l) D-biotinoyl-aminocaproic acid-N-hydroxysuccinimide ester (Boehringer Mannheim, order No. 1003933) and 0.5 g (2 mmol/l) mono-BOC-DADOO in 10 ml dioxane and 10 ml 0.1 mol/l potassium phosphate buffer pH 8.5 are stirred for ca. 2 hours at 20° C. After completion of the reaction (monitored by TLC: silica gel 60, eluant: ethyl acetate/methanol=3/7, RF=0.6) the solvent is removed by evaporation in a vacuum and 1 ml trifluoro acetic acid is added to the residue. It is stirred for ca. 30 minutes until the BOC group has been completely cleaved off. Subsequently the trifluoroacetic acid is removed by evaporation in a vacuum. 5 ml ethyl acetate is added to the residue, undissolved material is filtered off and the filtrate is evaporated to dryness. Yield: 0.96 g (98%)

TLC: silica gel 60, eluant: ethyl acetate/methanol=2:8, RF=0.2

EXAMPLE 27

Synthesis of S-acetyl-mercaptopropionic Acid 8.6 g (110 mmol) acetyl chloride is slowly added dropwise to 10.6 g (100 mmol) mercaptopropionic acid at 20° C. After completion of the addition it is heated for 10 min at 100° C. The reaction mixture is subjected to a vacuum distillation and the product is obtained in a pure form at 0.4 bar and 105° C.

Yield: 5.8 g (36%)

1-H-NMR (CDCl$_3$): δ (ppm)=2.3 (s, 3H), 2.7 (t, 2H), 3.1 (t, 2H).

EXAMPLE 28

Synthesis of N-succinimidyl-S-acetylthiopropionate, (SATP)

16.2 g (0.1 mol) S-acetyl-mercaptopropionic acid, 12.7 g (0.11 mol) N-hydroxysuccinimide and 22.7 g (0.11 mol) dicyclohexylcarbodiimide are stirred in 0.4 l absolute ethyl acetate for 16 hours at 20° C. The precipitate which forms is filtered off and the filtrate is evaporated in a vacuum. The oily residue is taken up in a small amount of ethyl acetate and cooled. In this process further precipitate is formed which is discarded. This process is repeated twice. 13 g (50%) SATP is obtained from the last filtrate after evaporation.

1H-NMR (CDCl$_3$): δ (ppm)=2.3 (s, 3H), 2.8 (s, 4H), 2.9 (m, 2H), 3.1 (m, 2H).

EXAMPLE 29

Synthesis of biotin-aminocaproic acid-amidodioxaoctylmercaptopropionic acid-amide, (Biotin Compound 7)

A solution of 0.96 g (2 mmol) biotin-X-DADOO (from example 26) and 0.5 g (2 mmol) SATP (from example 28) are stirred in 20 ml dioxane and 20 ml 0.1 mol/l potassium phosphate buffer pH 8.5 for 2 hours at 20° C. Subsequently the solution is evaporated to dryness, the residue is taken up with 2 ml trifluoroacetic acid and stirred under inert gas for 0.5 hours at 20° C. The purification is carried out by flash chromatography on silica gel.

(Eluant: ethyl acetate/methanol=3:7).

Yield: 150 mg (13%)

TLC: silica gel 60, ethyl acetate/methanol=3/7, RF=0.35

EXAMPLE 30

Synthesis of biotinamido-3,6-dioxaoctyl-S-acetylmercaptopropionic acid, (biotin-DADOO-SATP)

A solution of 1.4 g (5.35 mmol) SATP (from example 28) in 40 ml dioxane is added slowly to 1 g (2.7 mmol) biotin-DADOO dissolved in 40 ml 0.1 mol/l potassium phosphate buffer pH 7.0. During the addition the pH value has to be continuously readjusted with 0.1 mol/l potassium phosphate buffer to pH 7.0. After completion of the addition, it is stirred for a further 10 min and subsequently evaporated to dryness. The crude product can be used in the following step without purification. TLC: silica gel 60, eluant: ethyl acetate/methanol=3.5/7.5, RF=0.35.

EXAMPLE 31

Synthesis of bis-(biotinamido-3,6-dioxaoctyl) mercaptopropionic acid-amide-disulfide, (Biotin Compound 8)

1.6 g of the crude product of example 30 is dissolved in 100 ml of nitrogen-saturated 0.5 mol/l potassium phosphate buffer pH 7.5 and admixed with 5.4 ml 1 mol/l methanolic hydroxylamine solution. It is stirred for 2 hours at 20° C., subsequently evaporated to dryness in a vacuum and purified by flash chromatography on silica gel (ethyl acetate/methanol=3/7).

Yield: 150 mg (6%)

TLC: silica gel 60, eluant: ethyl acetate/methanol=3/7, RF=0.35

EXAMPLE 32

Synthesis of biotinamido-3,6-dioxaoctyl-S-acetylmercaptoacetic acid-amide, (biotin-DADOO-SATA)

The production is carried out analogous to example 30 from 187 mg (0.8 mmol) N-succinimidyl-S-acetylthioacetate (SATA) (Boehringer Mannheim, Order No. 1081765) and 300 mg (0.8 mmol) biotin-DADOO.

Yield: 109 mg (49%)

TLC: silica gel 60, eluant: ethyl acetate/methanol=6.5/3.5, RF=0.35

EXAMPLE 33

Synthesis of bis-(biotinamido-3,6-dioxaoctyl) mercaptoacetic acid-amide-disulfide, (Biotin Compound 9)

The production is carried out analogous to example 31 from 100 mg (0.2 mmol) biotin-DADOO-SATA and 0.25 ml 1 mol/l methanolic hydroxylamine solution.

Yield: 55 mg (60%).

TLC: silica gel 60, eluant: ethyl acetate/methanol=3/7, RF=0.35

EXAMPLE 34 a) 2-(S-acetyl)mercaptopropionic acid-2-(2-hydroxyethoxy) ethyl amide

A solution of 5 g (20 mmol) N-succinimidyl-S-acetyl thiopropionate (SATP, example 28) in 50 ml THF was added dropwise to a solution of 2.14 g (20 mmol) 2-(2-amino ethoxy)-ethanol in 25 ml THF within 15 min. and stirred for 2 hours at 20° C. Upon completion of the reaction (TLC control) the reaction mixture was evaporated in a vacuum and purified by chromatography on silica gel (silica gel 60, eluant:ethylacetate/methanol=7:3 plus 1% acetic acid)

TLC: (silica gel 60, eluant:ethylacetate/methanol=7:3 plus 1% acetic acid)

R$_f$=0.67 yield: 2.7 g

MS (pos FAB): MH⁺=2.36 b) 2-mercaptopropionic acid-[2-(2-hydroxyethoxy)]-ethylamide (Compound 10)

600 ml of a 1 mol/l solution of hydroxyl amine in methanol were added to 2.7 g (8.7 mmol) of the compound a) and stirred for one hour at 20° C. Then the solvent was evaporated in a vacuum and the residue was three times extracted with dichloromethane. 1.5 g oily crude product was obtained and purified by flash-chromatography on silica gel (silica gel 60, eluant: dichloromethane/methanol=9.3/0.7).

TLC: (silica gel 60, eluant: dichloromethane/methanol= 9/1)

$R_f$=0.45 yield: 0.86 g (colourless oil)

MS (pos FAB): MH⁺=194.

EXAMPLE 35

Production and Characterization of Monolayers a) Sample Preparation

The gold-substrates were prepared by depositing about 50 nm Au (99.99%) from the vapour phase on microscop slides from LASFN 9 (Berliner Glas KG).

The deposition was carried out in a vaporization device BAE 250 from Balzers at a pressure of $\leq 5 \times 10^{-6}$ mbar.

b) Monolayer-formation

The gold-substrates were placed into 0.5 mmol/l solutions of the respective compounds in water (milliQ) under argon protective gas immediately after the opening of the vaporization device. After a 6-hour adsorption period the substrates were rinsed with 300 ml water and dried in a nitrogen stream.

c) Characterization

The characterization of the monolayer was carried out by surface plasmon spectroscopy and by the method of contact angle determination.

Surface plasmon-spectroscopy is an optical method having a high sensitivity for the characterization of surfaces and thin films without requiring a specific molecule label (e.g. fluorescence label) (W. Knoll, MRS Bulletin, Vol. 16, No. 7, 1991, 29–39) hereby incorporated by reference.

Measurements against air and aqueous medium were carried out for the determination of the layer-thickness of the self-assembling monolayer (SAM).

Contact-angle determinations are a frequently used method for the analysis of interfaces. Thereby information relating to the substrate, the nature and composition of the cover and the order on the film may be obtained (see A. Ullmann, "Introduction to ultrathin organic films", Academic Press, Inc. 1991) hereby incorporated by reference. A contact angle microscope G1 (Kryss/Hamburg) was used for the determination of the contact angles. All values shown in tables 2 and 3 represent the mean values from at least 6 determinations at different places on the carrier. Thereby the error is ±2 degrees.

In the experiments below the wetting properties of water which was purified by ultrafiltration (milliQ) was measured on the respective films.

TABLE 2

Measured layer-thicknesses and contact angles thickness d [Å] of SAM

| | d measured | d calculated[2] (perpendicular) | d calculated[2] (30° inclined) | n[4] | θa[3][°] |
|---|---|---|---|---|---|
| comp. 10 from water | 9 ± 2 | 13 | 11 | 1.50 | 26 ± 2 |
| comp. 7 from water | 33 ± 2 | 38 | 33 | 1.50 | 35 ± 2 |
| comp. 7 from buffer[1] | 33 ± 2 | 38 | 33 | 1.50 | |

[1]phosphate buffer 0.05 mol/l, pH 7.0
[2]thickness of SAM calculated from bond length
[3]θa[°] determined according to A. Ullmann, "Introduction to ultrathin organic films", Academic Press, Inc. 1991.
[4]refractory index n according to Ullmann, supra The measured thicknesses are in good accordance with the theoretically calculated values. This indicates that ordered, tightly packed monolayers are present. Thereby the molecules should be inclined by about 30° to the surface normal in analogy to the data relating to long-chained alkanthiols published by Whitesides et al. (C. D. Bain, G. M. Whitesides, Science 240 (1988) 62; K. L. Prime, G. M. Whitesides, Science 252 (1991) 1164) hereby incorporated by reference.

Also the contact angles are in good accordance with the values of OH— or biotin-terminated alkanthiols on polycrystalline Au (L. Häussling, Dissertation Universität Mainz 1991). They support the image of ordered and tightly packed monolayers.

For the study of the streptavidin (SA)-binding ability of this novel class of compounds there were examined besides the pure biotin compound 7 also mixtures with dilution compound 10. Further, additional protein layers were built up by adsorption of biotinylated Fab-fragments of monoclonal antibodies against HCG (Fab<HCG>). Streptavidin and Fab were added as $5 \times 10^{-7}$ mol/l solutions and HCG (human choriogonadotropin) was added as 25 μg/ml solution in 0.5 mol/l NaCl.

TABLE 3

Measured contact angles θa and layer thicknesses d [Å]

| $X_b^1$ | θ[°][2] | d(SAM)[6] | D(SA)[3,7] | d(B-Fab)[4,7] | d(HCG)[7] | D(BSA)[5,7] |
|---|---|---|---|---|---|---|
| 0 | 26 ± 2 | 9 | 0 | 0 | | 0 |
| 0.1 | 37 ± 2 | 10 | 40 | 31 | 16 | |
| 0.25 | 40 ± 2 | 20 | 41 | 26 | 14 | |
| 0.50 | 39 ± 2 | 24 | 36 | 23 | 12 | |
| 0.75 | 39 ± 2 | 28 | 31 | 10 | 4 | |
| 1.00 | 35 ± 2 | 33 | 23 | 7 | 5 | |

[1]molar fraction referring to compound 7

TABLE 3-continued

Measured contact angles θa and layer thicknesses d [Å]

| $X_b^1$ | $\theta[°]^2$ | $d(SAM)^6$ | $D(SA)^{3,7}$ | $d(B-Fab)^{4,7}$ | $d(HCG)^7$ | $D(BSA)^{5,7}$ |
|---|---|---|---|---|---|---|

[2]θa[°] determined according to Ullmann, supra
[3]SA = streptavidin
[4]B-Fab = biotinylated Fab <HCG>.
[5]by means of addition of bovine serum albumin (BSA) an adsorption of the protein on free sites of the Au surface and consequently an increase in layer thickness would have been observed if the Au surface was incompletely covered by compounds 7 and 10.
[6]refractory index of the film: n = 1.50 (Ullmann, supra)
[7]refractory index of the film: n = 1.45 (H. Morgan, D. M. Taylor, C. D'Silva, Thin Solid Films 209 (1992) 122).

The thickness increase of the thiol monolayer d(SAM) correlates with the values of table 2.

By dilution of compound 7 on the gold surface with compound 10 a optimal streptavidin binding capability is obtained.

When the surface is completely covered with streptavidin the measured thickness is 40 Å and is thus in good accordance with the theoretically expected value (R. C. Ebersole, M. D. Word, J. A. Miller, J. R. Moran, J. Am. Chem. Soc. 112 (1990) 3239–3241; P. C. Weber, D. H. Ohlendorf, J. J. Wendoloski, F. R. Salemme, Science 242 (1989) 85).

This optimized streptavidin layer acts in turn as a optimal binding phase for B-Fab <HCG> which in turn may be used for the determination of HCG.

EXAMPLE 36

Regeneration of a Desthiobiotin Binding Matrix

The production of desthiobiotin monolayers is carried out according to example 23 from desthiobiotin compound 3 and 11-hydroxyundecanol. The mole fraction of desthiobiotin compound 3 in relation to 11-hydroxyundecanol is 0.1. The thickness is determined by surface plasmon resonance spectroscopy analogous to example 4. The desthiobiotin monolayer was incubated with streptavidin analogous to example 5 and with FAB<HCG> and HCG analogous to example 35. The regeneration of the desthiobiotin binding matrix was carried out by adding a solution of 2×10(−4) M biotin in 0.5M NaCl. Change of thickness of the resulting layers was again determined by surface plasmon resonance spectroscopy. Binding of streptavidin leads to a total covering of the desthiobiotin matrix which can be regenerated totally by adding biotin. The experiment can be repeated several times. Also a complex of streptavidin and further proteins can be displaced quantitatively by adding biotin.

It will be understood that the specification and examples illustrate but do not limit the present invention. Other embodiments within the spirit and scope of the invention will suggest themselves to those skilled in the art.

We claim:

1. A binding matrix comprising: a noble metal or noble metal oxide carrier material and a solid phase reactant wherein the solid phase reactant is adsorbed onto the noble metal or noble metal oxide carrier via thiol, disulphide or phosphine anchor groups, wherein the anchor groups have one or two solid phase reactant molecules attached per anchor group and are linked to the solid phase reactant via a flexible spacer molecule wherein the solid phase reactant is capable of binding to at least one free reaction partner and the solid phase reactant forms a dilute and essentially lateral homogeneous binding layer on the surface of the noble metal or noble metal oxide carrier material, and wherein the binding matrix further comprises other anchor groups not linked to the solid phase reactant.

2. The binding matrix of claim 1 wherein the coverage of the solid phase reactant on the surface of the carrier material is 0.1 to 90% of the maximum coverage.

3. The binding matrix of claim 2 wherein the coverage of the solid phase reactant on the surface of the carrier material is 0.5 to 70% of the maximum coverage.

4. The binding matrix of claim 3 wherein the coverage of the solid phase reactant on the surface of the carrier material is 1 to 40% of the maximum coverage.

5. The binding matrix of claim 1 wherein the carrier material has a gold, silver or palladium surface.

6. The binding matrix of claim 1 wherein the flexible spacer molecule contains at least one alkylene group having the formula $(CH_2)_n$ in which n is a number between 1 and 30.

7. The binding matrix of claim 6, wherein the spacer molecule is formed from cystamine.

8. The binding matrix of claim 1 wherein a straight-chained hydrophilic linker having a chain length of 4 to 15 atoms is between the spacer molecule and the solid phase reactant.

9. The binding matrix of claim 8 wherein the hydrophilic linker group contains at least one oxyethylene group.

10. The binding matrix of claim 9 wherein the hydrophilic linker group is formed by an amino terminal or hydroxyl-terminal polyethylene oxide.

11. The binding matrix of claim 10 wherein the hydrophilic linker group is formed from 1,8-diamino-3,6-dioxaoctane.

12. The binding matrix of claim 1 wherein the solid phase reactant is an antigen or hapten capable of binding to an antibody.

13. The binding matrix of claim 1 wherein the solid phase reactant consists of biotin or an analogous molecule which reacts with avidin or streptavidin together with avidin or streptavidin.

14. The binding matrix of claim 13 wherein the solid phase reactant consists of an inner biotin layer and an outer avidin or streptavidin layer wherein the outer layer is capable of binding to at least one free reaction partner.

15. The binding matrix of claim 14 wherein the inner biotin layer of the solid phase is an undiluted layer on the surface of the carrier material and the outer layer is coupled to the inner layer by affinity binding.

16. A method for determination of an analyte in a sample comprising contacting a solution containing said sample and a free reaction partner with the binding matrix of claim 1, wherein the solid phase reactant of said binding matrix and said free reaction partner have bioaffinity for each other, and determining binding between said free reaction partner and said solid phase reactant as a determination of said analyte.

17. The method of claim 16 wherein the specific binding reaction is determined optically, electronically, via heat tonality or mass analysis.

18. The method of claim 16 wherein the specific binding reaction is determined by optical reflection techniques.

19. The method of claim 18 wherein the specific binding reaction is determined by plasmon spectroscopy.

20. The method of claim 16 wherein the specific binding reaction is determined potentiometrically or amperometrically.

21. The method of claim 16 wherein the specific binding reaction is determined by means of the electrical conductivity or change in capacitance.

22. A process for the production of a binding matrix of claim 1 comprising incubating the carrier material with a reaction solution containing molecules which form the binding layer adsorbed to the carrier material.

23. A process for the production of a binding matrix comprising adsorbing a solid phase reactant onto a noble metal or noble metal oxide carrier material via anchor groups wherein the solid phase reactant is capable of binding to at least one free reaction partner, and wherein the solid phase reactant forms a dilute and essentially laterally homogeneous binding layer on the surface of the carrier material, and wherein the carrier material is incubated with an aqueous reaction solution comprising a hydrophilic dilution molecule and a solid phase reactant which is joined to the anchor group via a short-chained spacer molecule having at least one alkylene group $(CH_2)_n$ wherein n is a whole number from 1 to 30.

24. The process of claim 23 wherein the carrier material has a gold, silver or palladium surface and the anchor group is a thiol group, disulfide group or phosphine group.

25. The process of claim 23 wherein the anchor group is linked to the solid phase reactant via a flexible spacer molecule.

26. The process of claim 23 wherein the aqueous reaction solution is free from organic solvents and detergents.

27. The process of claim 23 wherein a hydrophilic linker group is located between the spacer molecule and the solid phase reactant.

28. The process of claim 27 wherein the hydrophilic linker group contains at least one oxyethylene group.

29. The process of claim 27 wherein the hydrophilic linker group is formed by an aminoterminal or hydroxyl-terminal polyethylene oxide.

30. The process of claim 27 wherein the hydrophilic linker group is formed from 1,8-diamino-3,6-dioxaoctane.

31. The process of claim 27 wherein a further spacer molecule is located between the hydrophilic linker group and the solid phase reactant.

32. The process of claim 23 wherein the hydrophilic dilution molecule comprises an anchor group and a spacer component.

33. The process of claim 32 wherein the hydrophilic dilution molecule additionally comprises a hydrophilic linker group.

34. The process of claim 32 wherein the dilution molecule is a compound of the formulae

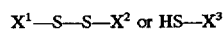

$X^1$—S—S—$X^2$ or HS—$X^3$ wherein $X^1$, $X^2$ and $X^3$ each represent n is a whole number from 1 to 6, L is a hydrophilic linker group with a chain length from 4 to 15 atoms and Y is a hydrophilic end group.

35. The process of claim 34 wherein the hydrophilic end group is —$NH_2$, —OH, —COOH or —$SO_3H$.

36. The process of claim 33 wherein the hydrophilic linker group comprises at least one oxyethylene group.

37. The process of claim 23 wherein the dilution molecule is 2-mercaptopropionic acid [2-(2-hydroxyethoxy)]-ethoxy)]ethylamide.

38. The process of claim 23 wherein the solid phase reactant is an antigen or hapten capable of binding to an antibody.

39. The process of claim 23 wherein the solid phase reactant is biotin or an analogous molecule which reacts with avidin or streptavidin.

40. The process of claim 23 wherein the solid phase reactant is a biotin derivative having a lower binding affinity to streptavidin compared with biotin.

41. The process of claim 39 wherein the free reaction partner that is capable of binding to the solid phase reactant is streptavidin, avidin.

42. The process of claim 23 wherein the binding matrix resulting from the adsorption of a solid phase reactant comprising anchor groups to the carrier material is incubated with at least one further substance consisting of biotin or an analagous molecule which reacts with avidin or streptavidin capable of binding with the binding matrix, whereby a solid phase reactant is produced consisting of several non-covalently linked compounds and wherein the binding pair are biotin or an analogous molecule bound to avidin or streptavidin.

43. The process of claim 16 further comprising regenerating a desthiobiotin binding matrix by removing the free reaction partner bound to the solid phase reactant from the desthiobiotin binding matrix by adding a further free reactant after determination of an analyte.

44. The process of claim 43 wherein the further free reactant has a higher affinity for the reaction partner than the solid phase reactant and the free reactant is desthiobiotin and the free reaction partner is streptavidin, avidin.

45. The binding matrix of claim 5 wherein the gold surface is bound to the carrier material surface via a binding mediator.

46. The binding matrix of claim 45 wherein the binding mediator is chromium.

47. The binding matrix of claim 45 wherein the binding mediator is about 0.1 to 10 nm thick.

48. The binding matrix of claim 5 wherein the gold, silver or palladium layer is about 10 to 100 nm in thickness.

49. The binding matrix of claim 9 wherein the linker group contains 1–5 oxyethylene groups.

50. The binding matrix of claim 8 wherein the linker group is a straight chain molecule having 4–15 atoms.

51. The binding matrix of claim 1 wherein the homogeneous binding layer on the surface of the carrier material is selected from the group of biotin, desthiobiotin and phenylhydantoin compounds selected from the group consisting of biotin compound 1
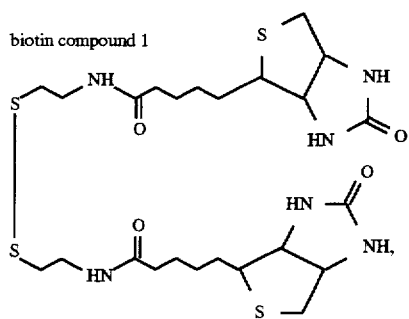
biotin compound 2
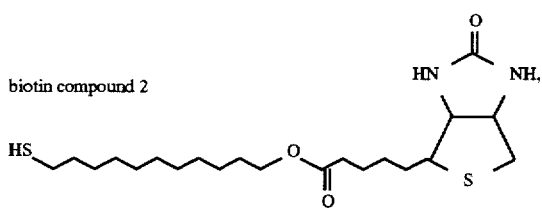
biotin compound 3
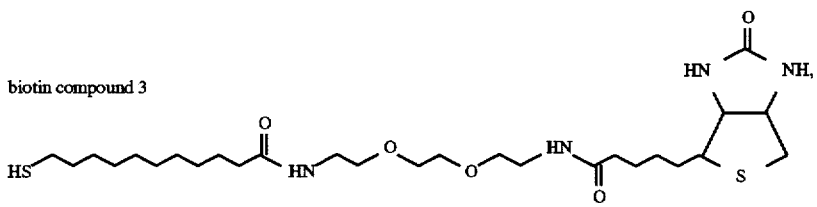
biotin compound 4
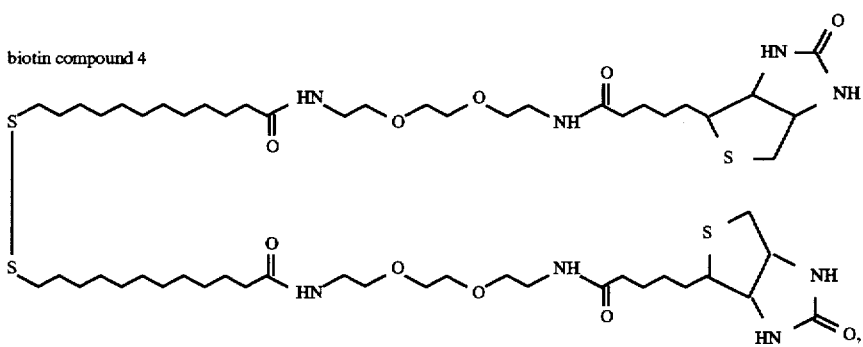
biotin compound 5
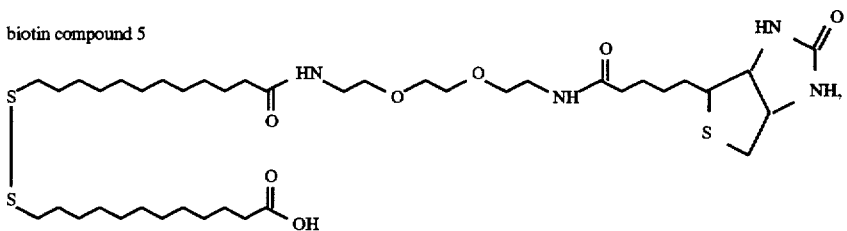
biotin compound 6
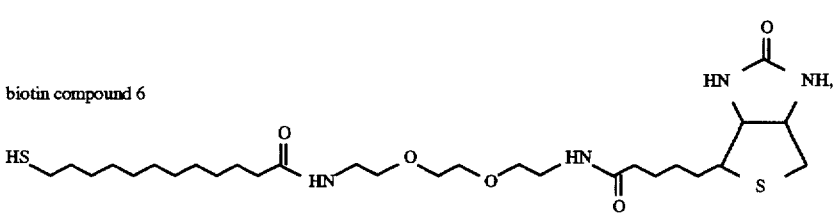

-continued
desthio compound 1
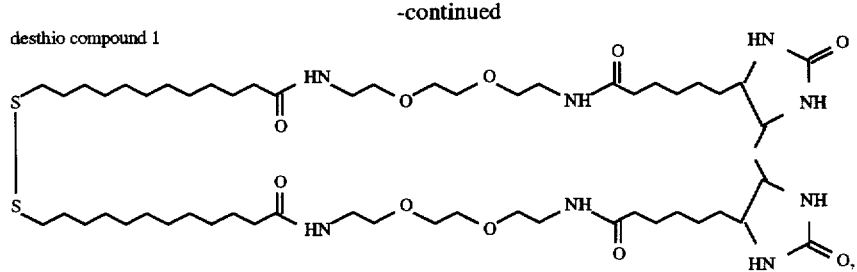
desthio compound 2
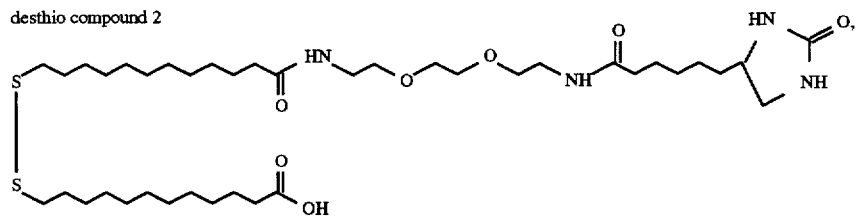
desthio compound 3
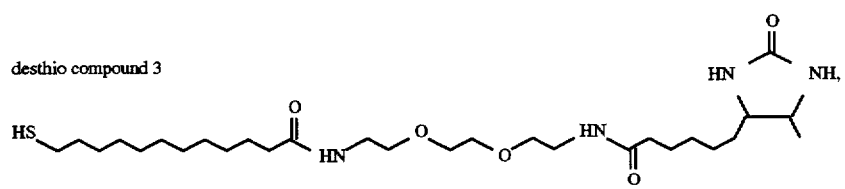
biotin compound 7
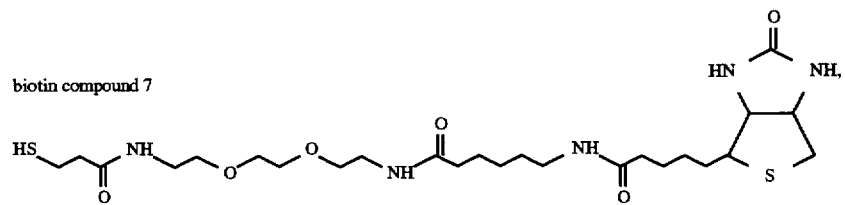
biotin compound 8
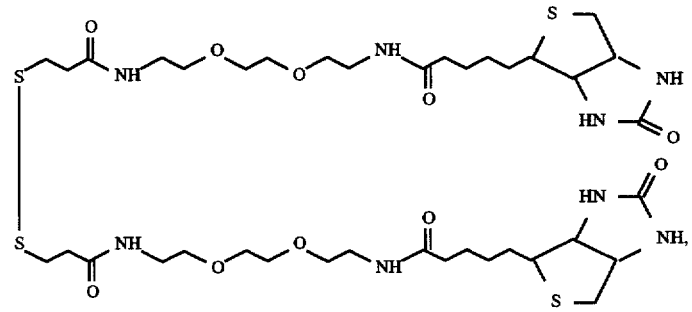
biotin compound 9
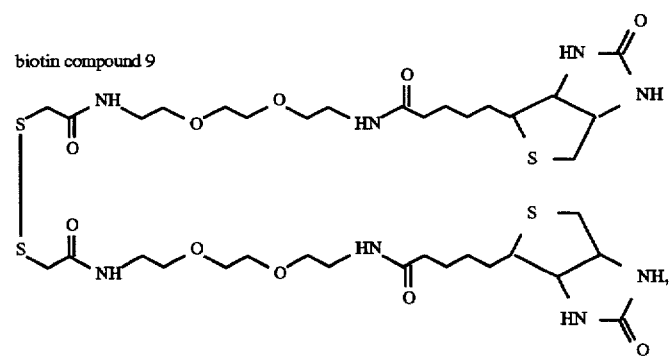

diphenylhydantoin compound

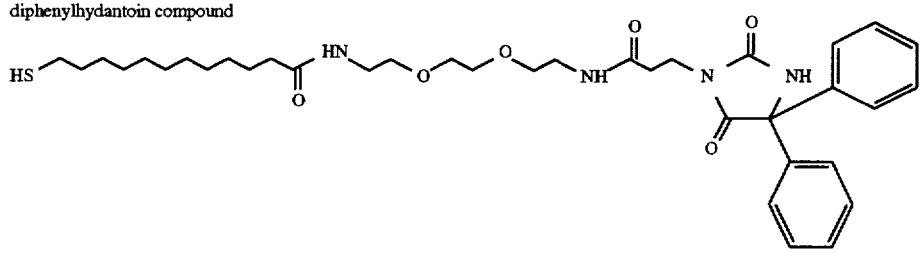

and compound 10

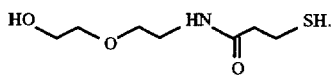

52. The binding matrix of claim 51 wherein the binding layer is adsorbed onto a gold surface.

53. The binding matrix of claim 1 wherein the solid phase reactant is selected from the group consisting of biotin, desthiobiotin, or iminobiotin and 4-hydroxy-phenyl-azobenzoic acid.

54. The method of claim 16 wherein the specific binding reaction is determined by indirect optical observation via an enzyme or fluorescent or luminescent label.

55. The binding matrix of claim 1 wherein the homogeneous binding layer on the surface of the carrier material is selected from the group consisting of desthio compound 1

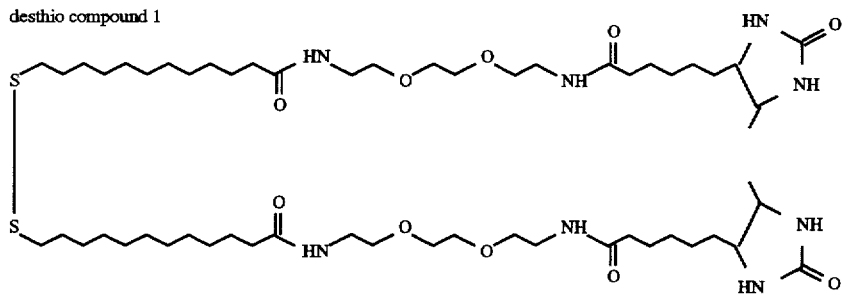

desthio compound 2

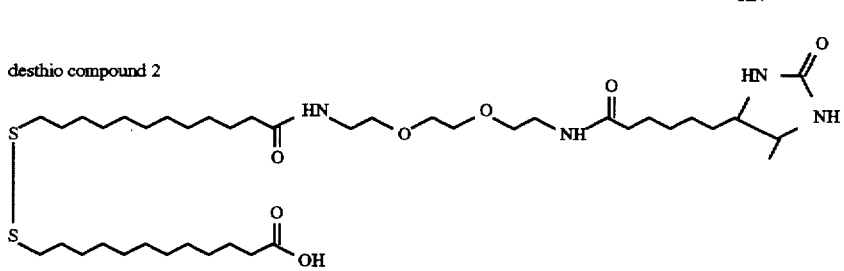

desthio compound 3

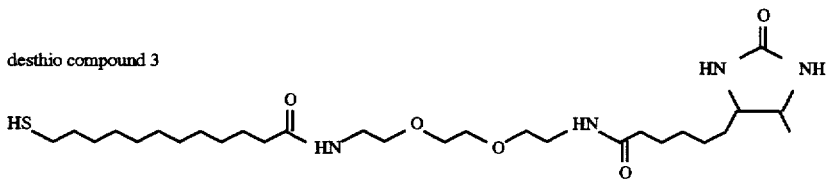

biotin compound 7

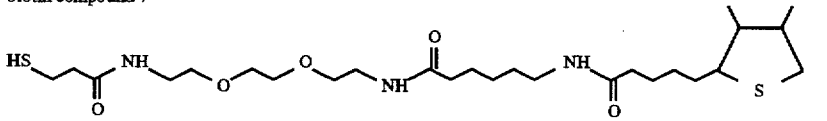

biotin compound 8

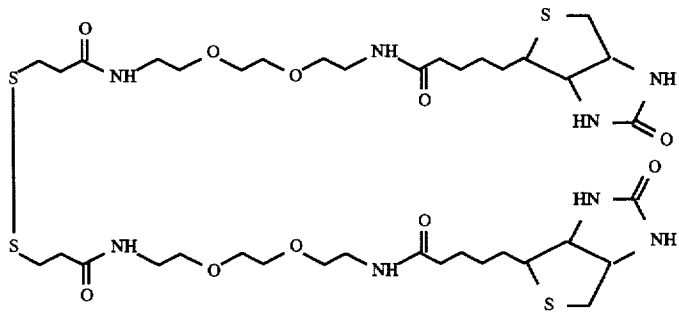

and biotin compound 9

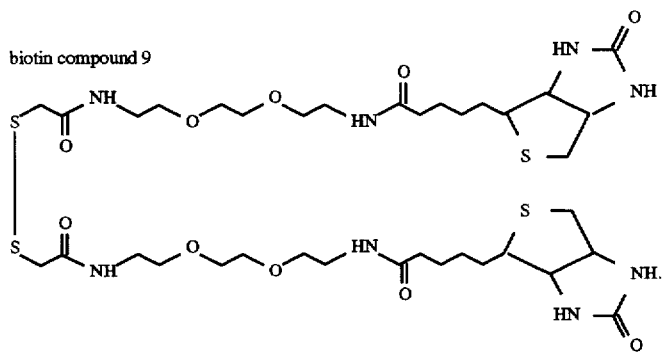

56. The binding matrix of claim 1 wherein said solid phase reactant is desthiobiotin which is capable of being regenerated by removing the free reaction partner bound to the solid phase reactant.

57. The binding matrix of claim 1 wherein the carrier material is selected from the group consisting of gold, silver, and palladium.

58. The method of claim 21, wherein a solid phase reactant is used which is a component of a binding matrix produced by adsorbing a solid phase reactant onto a noble metal or noble metal oxide carrier material via anchor groups wherein the solid phase reactant is capable of binding to at least one free reaction partner, and wherein the solid phase reactant forms a dilute and essentially laterally homogeneous binding layer on the surface of the carrier material, and wherein the carrier material is incubated with an aqueous reaction solution comprising a hydrophilic dilution molecule and a solid phase reactant which is joined to the anchor group via a short-chained spacer molecule having at least one alkylene group $(CH_2)_n$ wherein n is a whole number from 1 to 30.

* * * * *